United States Patent
Cedergreen

(10) Patent No.: US 12,039,608 B2
(45) Date of Patent: *Jul. 16, 2024

(54) METHODS AND SYSTEMS FOR MAINTAINING PHARMACY PROVIDER NETWORKS

(71) Applicant: Express Scripts Strategic Development, Inc., St. Louis, MO (US)

(72) Inventor: Jacob J. Cedergreen, St. Louis, MO (US)

(73) Assignee: Express Scripts Strategic Development, Inc., St. Louis, MO (US)

(*) Notice: Subject to any disclaimer, the term of this patent is extended or adjusted under 35 U.S.C. 154(b) by 342 days.

This patent is subject to a terminal disclaimer.

(21) Appl. No.: 17/405,818

(22) Filed: Aug. 18, 2021

(65) Prior Publication Data

US 2021/0374876 A1 Dec. 2, 2021

Related U.S. Application Data

(63) Continuation-in-part of application No. 16/509,721, filed on Jul. 12, 2019, now abandoned, which is a
(Continued)

(51) Int. Cl.
*G06Q 40/08* (2012.01)
*G06Q 50/22* (2024.01)

(52) U.S. Cl.
CPC .............. *G06Q 40/08* (2013.01); *G06Q 50/22* (2013.01)

(58) Field of Classification Search
CPC ........ G06Q 40/08; G06Q 50/22; G16H 20/10; G16H 40/20; G16H 40/67
See application file for complete search history.

(56) References Cited

U.S. PATENT DOCUMENTS 6,305,377 B1 10/2001 Portwood
7,698,155 B1 4/2010 Prasad
(Continued)

OTHER PUBLICATIONS

Member Central, "Pharmacy Networks," https://www.bluecrossma.com/wps/portal/members/using-my-plan/manage-my-plan/pharmacy-coverage/pharmacy-networks/!ut/p/ c4/04_SB8K8xLLM9MSSzPy8xBz9CP0os_gwRzMPJzcPlwP_QHM3A09vc6-gUNdAY4Ngl_2CbEdFACJNLOw!/ downloaded on Feb. 27, 2013, pp. 1.
(Continued)

*Primary Examiner* — Sheetal R Paulson
(74) *Attorney, Agent, or Firm* — The Small Patent Law Group

(57) ABSTRACT

Methods and systems for maintaining pharmacy provider networks are described. In one embodiment, claims adjudication data associated with a member and a prescribed drug is accessed. The prescribed drug associated with the member is classified as one of an acute medication and a maintenance medication. A pharmacy provider network is associated with the prescribed drug based on, at least in part, classifying the prescribed drug. It is determined if a pharmacy associated with the claims adjudication data is included within the pharmacy provider network associated with the prescribed drug. A pharmacy claim may be adjudicated for the prescribed drug based on the claim and the pharmacy provider network. Additional methods and systems are disclosed.

20 Claims, 9 Drawing Sheets

Related U.S. Application Data continuation of application No. 13/780,073, filed on Feb. 28, 2013, now Pat. No. 10,373,255.

(60) Provisional application No. 61/604,198, filed on Feb. 28, 2012.

(56) References Cited

U.S. PATENT DOCUMENTS

| | | | |
|---|---|---|---|
| 7,711,583 | B2 | 5/2010 | Epstein |
| 7,720,697 | B1 | 5/2010 | Silverstein |
| 8,055,511 | B2 | 11/2011 | McCallie |
| 8,386,274 | B1 | 2/2013 | Pinsonneault |
| 8,781,851 | B2 | 7/2014 | Anderson |
| 9,697,335 | B2 | 7/2017 | Joplin |
| 10,086,974 | B2 | 10/2018 | Joplin |
| 10,303,854 | B2 | 5/2019 | Joplin |
| 10,322,066 | B2 | 6/2019 | Thach |
| 10,331,858 | B2 | 6/2019 | Miller |
| 10,751,254 | B2 | 8/2020 | Joplin |
| 10,777,310 | B2 | 9/2020 | Joplin |
| 11,593,393 | B1 * | 2/2023 | Allor ............ G06Q 10/067 |
| 2003/0167189 | A1 | 9/2003 | Lutgen |
| 2004/0162740 | A1 | 8/2004 | Ericsson |
| 2006/0184391 | A1 | 8/2006 | Barre |
| 2007/0043589 | A1 | 2/2007 | Warren |
| 2007/0214009 | A1 | 9/2007 | Epstein |
| 2008/0275738 | A1 | 11/2008 | Shillingburg |
| 2009/0198517 | A1 | 8/2009 | Ruben |
| 2012/0053960 | A1 | 3/2012 | Gatti |
| 2012/0253846 | A1 | 10/2012 | Pramod |
| 2014/0222456 | A1 | 8/2014 | Abou Nader |
| 2016/0321406 | A1 | 11/2016 | Timmerman |
| 2019/0333158 | A1 | 10/2019 | Cedergreen |
| 2021/0374876 | A1 * | 12/2021 | Cedergreen ............ G06Q 10/10 |

OTHER PUBLICATIONS

Florida Blue, "Pharmacy Coverage," http://www3.bcbsfl.com/wps/portal/bcbsfl/!ut/p/c0/04_SB8K8xLLM9MSSzPy8xBz-9CP0os3gnA39DAwPHEEdXV3cnA89gr1AfZ88A139n1_2CbEdFABaCju4!/?WCM_PORTLET=PC_-7_B0O100ATAEEGB0lSJULCIP2CA3_WCM&WCM_GLOBAL_CONTEXT=/wps/wcm/connect/www_C- ontent/si_bcbsfl/sa_employers/sa_ourplans/sa_pharmacycoverage/ct_emp_ourpl- ans_pharmacy_benefitlistinghome, downloaded on Feb. 27, 2013, pp. 1-3.

United Healthcare, "Pharmacy Benefit Programs," http://consultant.uhc.com/assets/100-9999UHCPharmacyBenefitsASOSS4-11.pdf[p5], downloaded on Feb. 27, 2013, pp. 1-8.

BlueCross BlueShield of North Carolina, Specialty Pharmacy Networks Effective Jul. 1, 2011 Overview for BCBSNC Producers May 26, 2011, f.cfluent.com/f/3569/internet/1563_bcbs-specilaty-pharmacy-faqs.pdf, downloaded on Feb. 27, 2013, pp. 1-5.

PLOS One, Jul. 9, 2008, "Automated Identification of Acute Hepatitis B Using Electronic Medical Record Data to Facilitate Public Health Surveillance," http://www.ncbi.nlm.nih.gov/pmc/articles/PMC2440348/, downloaded on Feb. 27, 2013, pp. 1.

Wolters Kluwer Health—Medi-Span-Drug Indications Database, "Drug Indications Database," http://www.medispan.com/drug-indications-database.aspx, downloaded on Feb. 28, 2013, pp. 1-2.

HomeMD—Drug Reference for Medical Conditions for iPhone . . . , "Itunes is the worlds easiest way to organise and add to your digital media collection." http://itunes.apple.com/ke/app/ihomemd-drug-reference-for/id427865188?mt=8, downloaded on Feb. 27, 2013, pp. 1-2.

\* cited by examiner

METHODS AND SYSTEMS FOR MAINTAINING PHARMACY PROVIDER NETWORKS

CROSS-REFERENCE TO RELATED APPLICATIONS

This application is a continuation-in-part of U.S. patent application Ser. No. 16/509,721, filed on 12 Jul. 2019, which is a continuation of U.S. patent application Ser. No. 13/780,073, filed 28 Feb. 2013 (now U.S. Pat. No. 10,373,255), which claims priority to U.S. Provisional Patent Application No. 61/604,198, filed 28 Feb. 2012. The entire disclosures of these applications are incorporated herein by reference.

FIELD

The field relates to pharmacy benefit plans, and more particularly to pharmacy networks for different prescription types.

BACKGROUND

Pharmacy benefit managers generally provide prescription drug programs for clients that may, for example, sponsor drug benefit programs for members. As part of the providing the prescription drug programs for clients, pharmacy benefit managers (PBM's) may adjudicate claims from pharmacies for prescriptions filled by members at various pharmacies. The PBM may also reimburse the pharmacies for prescriptions obtained by members at the pharmacies. The PBM may also bill clients for the cost of prescriptions adjudicated by the pharmacy benefit manager.

BRIEF SUMMARY

In one embodiment, a method for communicating over a network to fill a prescription is provided. The method includes retrieving claims adjudication data associated with a member and a prescribed drug stored in the memory, and determining (on or using one or more processors) whether a number of available fills of the prescribed drug exceeds an acute medication threshold number of the available fills. The acute medication threshold number can be stored in a database and included in a pharmacy benefit provided to the member. The method also can include classifying (using the one or more processors) the prescribed drug associated with the member as an acute medication or a maintenance medication based on determining whether the number of the available fills exceeds the acute medication threshold number, associating (using the one or more processors) the prescribed drug with an acute medication pharmacy provider network or a maintenance medication pharmacy provider network based on classification of the prescribed drug, determining (using the one or more processors) whether a pharmacy associated with the claims adjudication data is included within the pharmacy provider network type that is associated with the prescribed drug, adjudicating (using the one or more processors) a pharmacy claim for the prescribed drug through the pharmacy based on the claims adjudication data and a determination of whether the pharmacy is included within the pharmacy provider network type, communicating an adjudication response indicative of the pharmacy claim that is adjudicated to an order processing device at a pharmacy filling system via a communication network, determining which automated dispensing devices of the pharmacy filling system are responsible for filling the prescribed drug associated with the pharmacy claim that is adjudicated based on the adjudication response, directing a pallet sizing and pucking device of the pharmacy filling system to arrange pucks on a pallet based on which of the automated dispensing devices is determined to be responsible for filling the prescribed drug, directing a loading device to load one or more prescription containers into the pucks on the pallet based on which of the automated dispensing devices is determined to be responsible for filling the prescribed drug, and automatically filling the prescription at the pharmacy after receipt of the adjudication response using an automated dispensing device dispensing the prescribed drug into one or more of the prescription containers.

In one embodiment, a non-transitory machine-readable medium storing instructions for filling a prescription over a network is provided. The instructions, when or while executed by one or more processors, cause the one or more processors to retrieve claims adjudication data associated with a member and a prescribed drug stored in the memory, and determine whether a number of available fills of the prescribed drug exceeds an acute medication threshold number of the available fills. The acute medication threshold number can be stored in a database and included a pharmacy benefit provided to the member. The instructions also can direct or cause the processor(s) to classify the prescribed drug associated with the member as an acute medication or a maintenance medication based on determining whether the number of the available fills exceeds the acute medication threshold number, associate the prescribed drug with an acute medication pharmacy provider network or a maintenance medication pharmacy provider network based on classification of the prescribed drug, determine whether a pharmacy associated with the claims adjudication data is included within the pharmacy provider network type that is associated with the prescribed drug, adjudicate a pharmacy claim for the prescribed drug through the pharmacy based on the claims adjudication data and a determination of whether the pharmacy is included within the pharmacy provider network type, communicate an adjudication response indicative of the pharmacy claim that is adjudicated to an order processing device at a pharmacy filling system via a communication network, determine which automated dispensing devices of the pharmacy filling system are responsible for filling the prescribed drug associated with the pharmacy claim that is adjudicated based on the adjudication response, direct a pallet sizing and pucking device of the pharmacy filling system to arrange pucks on a pallet based on which of the automated dispensing devices is determined to be responsible for filling the prescribed drug, direct a loading device to load one or more prescription containers into the pucks on the pallet based on which of the automated dispensing devices is determined to be responsible for filling the prescribed drug, and automatically fill the prescription at the pharmacy after receipt of the adjudication response using an automated dispensing device dispensing the prescribed drug into one or more of the prescription containers.

In one embodiment, a method for filling a prescription is provided. The method includes receiving (on or using one or more processors) a pharmacy claim to adjudicate the pharmacy claim associated with a member and a prescribed drug, selecting an acute medication threshold number of available fills, communicating the acute medication threshold number of available fills to the one or more processors, classifying (using the one or more processors) the prescribed drug associated with the member as a maintenance medication based on a determination of whether a number of available fills of the prescribed drug exceeds the acute medication threshold number of available fills, determining (using the one or more processors) that a pharmacy associated with a request to adjudicate the pharmacy claim is included within an acute medication pharmacy provider network, communicating (using the one or more processors) a warning that a modified set of member benefits are associated with filling the prescribed drug at the pharmacy based on classification of the prescribed drug as a maintenance medication and a determination that the pharmacy is included within the acute medication pharmacy provider network, and controlling a filling of the prescription for the member at the pharmacy after receipt of an adjudication response associated with the member. The filling of the prescription can be controlled by communicating an adjudication response indicative of the pharmacy claim that is adjudicated to an order processing device at a pharmacy filling system via a communication network, determining which automated dispensing devices of the pharmacy filling system are responsible for filling the prescribed drug associated with the pharmacy claim that is adjudicated based on the adjudication response, directing a loading device to load one or more prescription containers into pucks on a pallet based on which of the automated dispensing devices is determined to be responsible for filling the prescribed drug, and automatically filling the prescription at the pharmacy after receipt of the adjudication response using an automated dispensing device dispensing the prescribed drug into one or more of the prescription containers.

DETAILED DESCRIPTION

Figure 1:
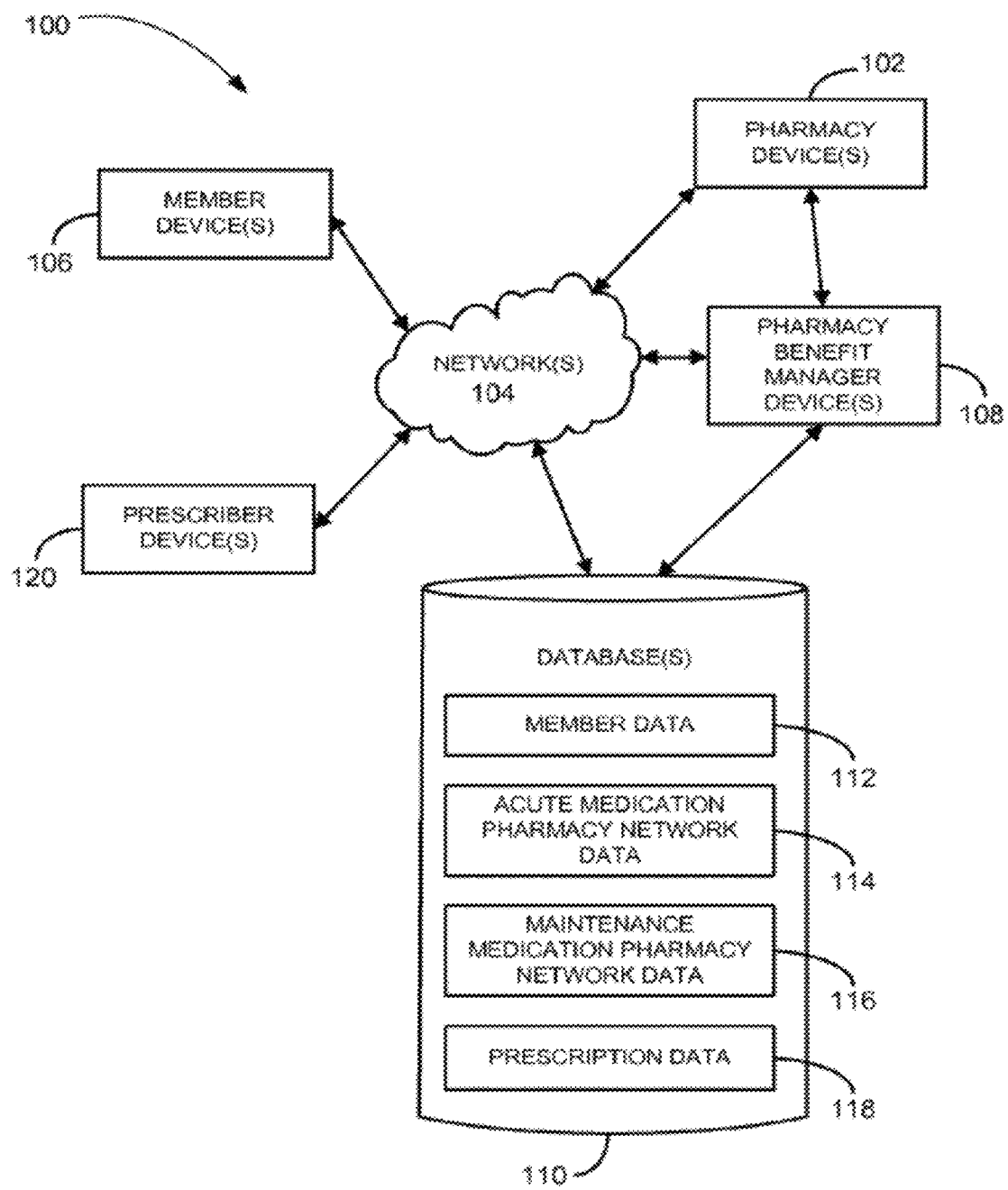
FIG. 1 is a block diagram of an example system, according to an example embodiment.

Example methods and systems for maintaining pharmacy provider networks are described. In the following description, for purposes of explanation, numerous specific details are set forth in order to provide a thorough understanding of example embodiments. It will be evident, however, to one of ordinary skill in the art that embodiments of the invention may be practiced without these specific details.

Generally, a client engages a PBM to offer a drug benefit program. Examples of clients include governmental organizations (e.g., Federal government agencies, the Department of Defense, the Centers for Medicare and Medicaid Services and state government agencies), middle market companies, large national employers, health insurance companies that have carved out the drug benefit, and the like. The PBM may be a stand-alone PBM, or may be part of a larger organization that offers other benefits or services. In conjunction with receiving the co-pay (if any) from the member and dispensing the prescribed drug to the member, a pharmacy submits a claim to the PBM for the prescribed drug. The PBM may perform certain adjudication operations including verifying the eligibility of the member, reviewing the formulary to determine appropriate co-pay, coinsurance, and deductible for the prescribed drug, and performing a drug utilization review (DUR) on the member. In some embodiments, the PBM may determine and/or classify the prescribed drug and associate the drug with an acute medication pharmacy provider network or a maintenance medication pharmacy provider network.

The PBM may then provide a response to the pharmacy following performance of the aforementioned operations. As part of the adjudication, the client (or the PBM on behalf of the client) may ultimately reimburse the pharmacy for filling the prescribed drug when the prescription drug claim was successfully adjudicated. The aforementioned adjudication operations generally occur before the co-pay is received and the prescribed drug dispensed. However, the operations may occur simultaneously, substantially simultaneously, or in a different order. In addition, more or less adjudication operations may be performed as part of the adjudication process.

The methods and systems described herein may be used for maintaining pharmacy provider networks and, optionally, automatically filling prescriptions responsive to adjudicating claims as set forth herein. In some instances, a prescriber, such as a doctor or other medical services provider, may prescribe a course of treatment that includes prescription drugs or medications. If the prescribed drug is to be used for a relatively short period of time, the prescribed drug may be referred to as an acute medication. Examples of acute medications may include, but are not limited to, anti-depressants, anti-viral mediations, muscle relaxants, antibiotics, and decongestants. If the prescribed drug is to be used for a relatively longer period of time and/or meets a certain criterion, the prescribed drug may be referred to as a maintenance medication or a maintenance drug. The relatively short period of time and relatively long period of time may, in some embodiments, generally reflect the number of times that the prescription associated with the prescribed drug will be/has been filled. For example, a relatively short period of time may reflect that the prescribed drug is filled a single time or two times, while a relatively long period of time may reflect that the prescribed drug is filled more than two times. The number of fills associated with a relatively short period of time and a relatively long period of time may vary according to different embodiments and/or circumstances. In some instances, maintenance medication may be used to treat a chronic disease state and may be administered continuously rather than intermittently. Therapy with maintenance medication may not be considered curative or promoting of recovery. Some examples of maintenance medication may include, but are not limited to, hormone therapies, diabetes medication, heart medication, seizure medication, and osteoporosis medication.

In some instances, acute medication may be associated with a higher initial cost burden. For example, a pharmacy dispensing the prescribed drug for the patient may require the pharmacist to spend time obtaining information from the patient (e.g., benefit information, medical history, or the like) or educating the member about the prescribed drug. The cost associated with dispensing the prescribed drug may decrease with successive fills for the same prescribed medication for the same patient (e.g., if the medication is a maintenance medication), where the pharmacist typically spends less time educating the patient about the prescribed drug or gathering information associated with the patient, after initial consultations. For example, a pharmacist may initially (e.g., when the patient requests a first or second fill of the prescription) spend a similar amount of time obtaining information from the patient, educating the patient, etc., for prescriptions for maintenance medications and acute medications. After such initial time expenditure, however, the pharmacist may not be required to engage the patient in such depth for continuing refills of the maintenance medication.

In some embodiments, maintaining separate pharmacy provider networks may provide clients with more competitive reimbursement rates. These more competitive rates may be reduced, potentially resulting in reduced cost to patients for prescription drugs.

FIG. 1 is a block diagram of an example system 100, according to an example embodiment. The system 100 may include a pharmacy device 102 in communication over a network 104 with a member device 106. Similarly, one or more of the pharmacy device 102 and the member device 106 may be in communication with a pharmacy benefit manager device 108 over a network 104. Other devices may also be included.

In an embodiment, the pharmacy device 102 may be a device associated with the retail pharmacy location at which a patient attempts to obtain a prescribed drug. In some embodiments, the pharmacy device 102 may be associated with a mail order pharmacy or other drug dispensing location or service. The pharmacy device 102 may be utilized by the pharmacy, for example to submit a claim associated with a prescription to be filled to the PBM for adjudication. Additionally, in some embodiments, the pharmacy device 102 may enable reimbursement of the pharmacy by the PBM (e.g., on behalf of the client sponsoring the drug benefit program) for the prescription obtained by the patient.

The member device 106 may be a device operated by an entity that enables members of a drug benefit program offered by the PBM to access member benefits data and claims history data (e.g., for the member and the member's family). In some embodiments, the member device 106, alone and/or in conjunction with one or more other devices, may facilitate filling prescriptions (e.g., requesting prescription fills via a pharmaceutical delivery channel, automatically filling prescriptions, etc.) by a member of a drug benefit program. In some embodiments, the member need not use the member device to obtain prescription drugs fills.

The pharmacy benefit manager device 108 is a device, or more than one device, operated by an entity at least partially responsible for the creation and/or management of drug benefit programs. While the pharmacy benefit manager device 108 is typically operated by a PBM, other entities may operate the pharmacy benefit manager device 108 either on behalf of themselves, the PBM, or another entity. In some embodiments, a benefit manager that provides the drug benefit may also provide one or more than one additional benefits including a health benefit, a dental benefit, a vision benefit, a wellness benefit, a radiology benefit, a pet care benefit, an insurance benefit, a long term care benefit, a nursing home benefit, and the like.

In general, a client engages a PBM to offer a drug benefit program. A person who is a participant or member of a drug benefit program offered by the client may obtain prescription drugs according to pricing, pharmacy selection, rebates, discounts, and the like, provided by the terms of the drug benefit program. The PBM may offer various therapy implementation programs that may impact the pricing, pharmacy selection, rebased, discounts, and the like, provided to members of the drug benefit plan.

The client's offered drug benefit program may be a stand-alone drug benefit operated by the PBM, or as part of a health care benefit operated by a health insurance company where the PBM services are offered directly by the health insurance company or offered indirectly by the PBM on behalf of the health insurance company.

The PBM may service a variety of people in a single drug benefit program, multiple drug benefit programs, or may otherwise service people. In some embodiments, the pharmacy benefit manager device 108 may be generally capable of analyzing claim adjudication data associated with members to identify one or more prescribed drugs associated with the member. In some embodiments, the claim adjudication data may be received through an adjudication request for a pharmacy claim. In some embodiments, the adjudication request may be received from a pharmacy device 102.

The pharmacy benefit manager device 108 (and/or another device) may be in communication directly (e.g., through local storage) and/or through the network 104 (e.g., in a cloud configuration or software as a service) with a database 110. The database 110 may be deployed, in whole or in part, on one or more of the pharmacy device 102, the member device 106, the pharmacy benefit manager device 108 and/or on another device. The database 110 may store one or more of member data 112, acute medication pharmacy network data 114, maintenance medication pharmacy network data 116, and/or prescription data 118.

The member data 112 may include information regarding members of the drug benefit program. In general, the member data 112 may include various data regarding members of a drug benefit program administered by the PBM. For example, the member data 112 may include member name, member contact information (e.g., address, telephone number, email address, and the like), member health related information, member demographic information. In some embodiments, the member data may include member claims data for claims that have been adjudicated for each member of a drug benefit program (e.g. prescribed drugs, prescription history, pharmacy usage, co-pay information, and the like). The member data 112 may include current and/or historical claims adjudication data for members of the drug benefit program, including prescriptions filled by a member, number of fills of each prescription for the member, dates of fills of each prescription for the member, drug utilization reviews for each prescription for the member, an identification of each pharmacy at which each fill of each prescription was obtained, and the like.

The acute medication pharmacy network data 114 may include data associated with an acute medication pharmacy network. Such data may include, for example, pharmacy providers that belong to an acute medication pharmacy network associated with a drug benefit program, costs associated with the acute medication pharmacy network and with pharmacy providers that belong to the acute medication pharmacy network, criterion for establishing a prescribed drug as an acute medication, and the like.

The maintenance medication pharmacy network data 116 may include data associated with maintenance medication pharmacy network. Such data may include, for example, pharmacy providers that belong to a maintenance medication pharmacy network, costs associated with the maintenance medication pharmacy network and with pharmacy providers that belong to the maintenance medication pharmacy network, criterion for establishing a prescribed drug as a maintenance medication, and the like.

Prescription data 118 may include data associated with prescriptions filled by one or more members of the drug benefit program, for example, an identification of the member and the prescribed drug, an identification of one or more pharmacies at which a prescription, or more than one prescriptions, for the drug have been filled, an identification of the dates on which the prescription(s) have been filled, a quantity of drug filled, an identification of the healthcare professional that prescribed the drug, and the like. In some embodiments, the prescription data 118 may include prescription drug claims that have submitted to the PBM by one or more pharmacies and/or prescription drug claims that have been adjudicated by the PBM. As such, the prescription data 118 may include information collected and/or utilized in connection with adjudicating a pharmacy claim for a prescription. The prescription data 118 may also include the results of adjudicating a claim (e.g., claim approval, claim denial, as well as any additional information). The prescription data 118 may include prescription data that maybe stored by one or more devices in FIG. 1.

A prescriber device 120 may also be coupled to the network 104 for communication with one or more other devices, such as the pharmacy device 102, the member device 106, and the pharmacy benefit manager device 108. The prescriber device 120 may be operated by, or on behalf of, a medical care professional that may prescribe a course of treatment that may include a prescribed drug for a member. In some embodiments, the prescriber device 120 may be utilized by the medical care professional to transmit a prescription associated with a patient (who may be a member of the drug benefit program) to a pharmacy (e.g., via the pharmacy device 102) and/or to the pharmacy benefit manager device 108. The pharmacy, to which the prescription may be transmitted, may be a retail pharmacy location, a mail order pharmacy, or another type of drug dispensing facility.

In the system 100, the pharmacy device 102, the member device 106, and/or the prescriber device 120 may communicate with the pharmacy benefit manager device 108 to enable a member to have a prescription filled through a pharmaceutical delivery channel. The pharmaceutical delivery channel may include, for example, a retail pharmacy location, a mail order pharmacy service, or other drug dispensing service. In some embodiments, the prescriber device 120 may be used to send and receive information including the prescription data 118 associated with a member. The person operating the member device 106 may be a member of a drug benefit plan operated by the PBM, and who has a drug prescribed to them by a medical healthcare professional, and/or may be an individual (such as a family member, care giver, or the like) who may operate the member device 106 on behalf of the individual who has received a prescription for a drug. The member device 106 may be associated with a single member, or multiple members. A member may use multiple member devices 106.

Examples of the network 104 by which the pharmacy device 102, the member device 106, the pharmacy benefit manager device 108, and the prescriber device 120 may communicate with one or more of each other may include Mobile Communications (GSM) network, a code division multiple access (CDMA) network, 3rd Generation Partnership Project (3GPP), an Internet Protocol (IP) network, a Wireless Application Protocol (WAP) network, a WiFi network, or an IEEE 802.11 standards network, as well as various combinations thereof. Other conventional and/or later developed wired and wireless networks may also be used.

While the system 100 in FIG. 1 is shown to include single devices 102, 106, 108, and 120, multiple devices may be used. Examples of the devices 102, 106, 108, and 120 include a server computer, a personal computer, a laptop or notebook computer, a mobile computing device (such as a smartphone, a tablet computing device, a personal digital assistant (PDA), or the like), a display device, a generic or specialized computing system, a gaming unit, or the like. Other devices may also be used. The devices 102, 106, 108, and 120 may each be the same type of device, or may be different types of devices.

Additionally, while the system 100 is shown to include a single network (i.e., the network 104) in FIG. 1, multiple networks may be used. The multiple networks may communicate with one another, e.g., as in series to link the devices 102, 106, 108, 120, or in parallel to link the devices 102, 106, 108, 120.

Figure 2:
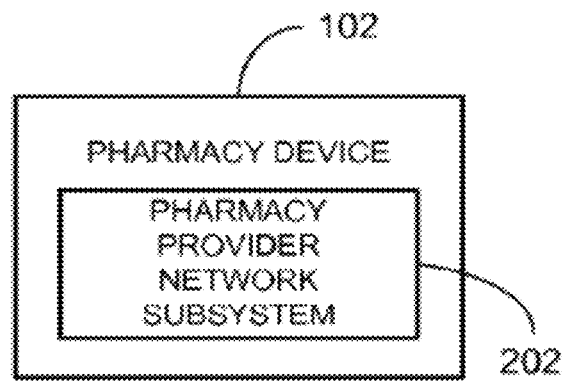
FIG. 2 illustrates an example pharmacy device that may be deployed in the system of FIG. 1, according to an example embodiment.

FIG. 2 illustrates the pharmacy device 102, according to an example embodiment. The pharmacy device 102 may be deployed in the system 100, and/or may be otherwise deployed. The pharmacy device 102 may be used by a device operator to submit claims information to the pharmacy benefit manager device 108. The claims information may be associated with a prescription that a member is attempting to fill at the pharmacy operating the pharmacy device 102. The claims information may be submitted (e.g., via transmission between the pharmacy device 102 and the pharmacy benefit manager device 108) to the pharmacy benefit manager device 108 for adjudication of the claim, e.g., to determine eligibility and coverage of the prescription under the drug benefit program, the deductible amount for which the member is responsible, and the like.

The pharmacy device 102 may include a pharmacy provider network subsystem 202. In general, the pharmacy provider network subsystem 202 may enable a PBM to associate an identified prescribed drug with the appropriate pharmacy provider network. For example, in some embodiments the pharmacy provider network subsystem 202 may allow a PBM to identify a particular prescription for a particular drug as being a prescription for an acute medication. In some embodiments, the pharmacy provider network subsystem 202 may allow a PBM to identify a particular prescription for a particular drug as being a prescription of a maintenance medication. In some embodiments, the pharmacy provider network subsystem 202 may allow a PBM to associate prescriptions for acute medications with an acute medication provider network. In some embodiments, the pharmacy provider network subsystem 202 may allow a PBM to associate prescriptions for maintenance medications with a maintenance medication provider network. Further, in some embodiments the pharmacy provider network subsystem 202 may allow a PBM to establish acute medication provider networks including specifically and/or generally identified pharmacies, and to establish maintenance medication provider networks including specifically and/or generally identified pharmacies. In some embodiments, the pharmacy provider network subsystem 202 may allow a PBM to establish eligibility and/or coverage benefits for prescriptions of acute medications and maintenance medications filled at pharmacies included within acute medication provider networks or maintenance medication provider networks.

Figure 3:
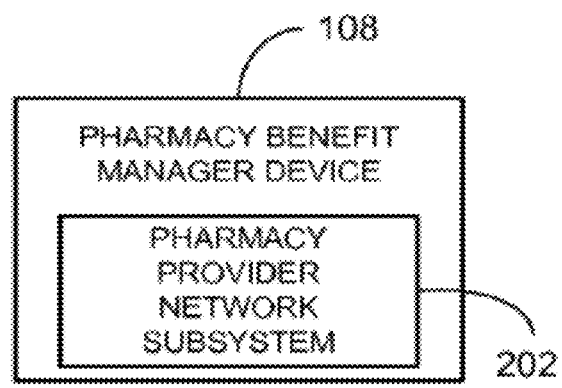
FIG. 3 illustrates an example pharmacy benefit manager device that may be deployed in the system of FIG. 1, according to an example embodiment.

FIG. 3 illustrates the pharmacy benefit manager device 108, according to an example embodiment. The benefit manager device 108 may be deployed in system 100 and/or may be otherwise deployed. In general, the pharmacy benefit manager device 108 may allow a PBM to receive claims information (e.g., from a pharmacy device 102 via the network 104) from a pharmacy. The claims information may be associated with a prescription submitted to the pharmacy by a member of a drug benefit program administered by the PBM. The claims information may allow the PBM to adjudicate the claim of the prescription, e.g., to determine eligibility of the member, review the formulary, determine appropriate co-pay by the member for the prescription, perform drug utilization review, and/or to perform other pharmacy claims adjudication functions.

The pharmacy benefit manager device 108 may include a pharmacy provider network subsystem 202. In some embodiments, the pharmacy provider network subsystem 202 included within the pharmacy benefit manager device 108 may provide server-side functionality to the pharmacy device 102. By way of example, the pharmacy provider network subsystem 202 may be deployed in the pharmacy device 102 and the pharmacy benefit manager device 108. In some embodiments, the pharmacy device 102 may perform a portion of the operations described herein, and the PBM device 108 may perform a portion of the operations described herein. In some embodiments, all of the functionality of the pharmacy provider network subsystem 202 may be provided by the pharmacy device, may be provided by the pharmacy benefit manager device 108, or may be provided by another device.

Figure 4:
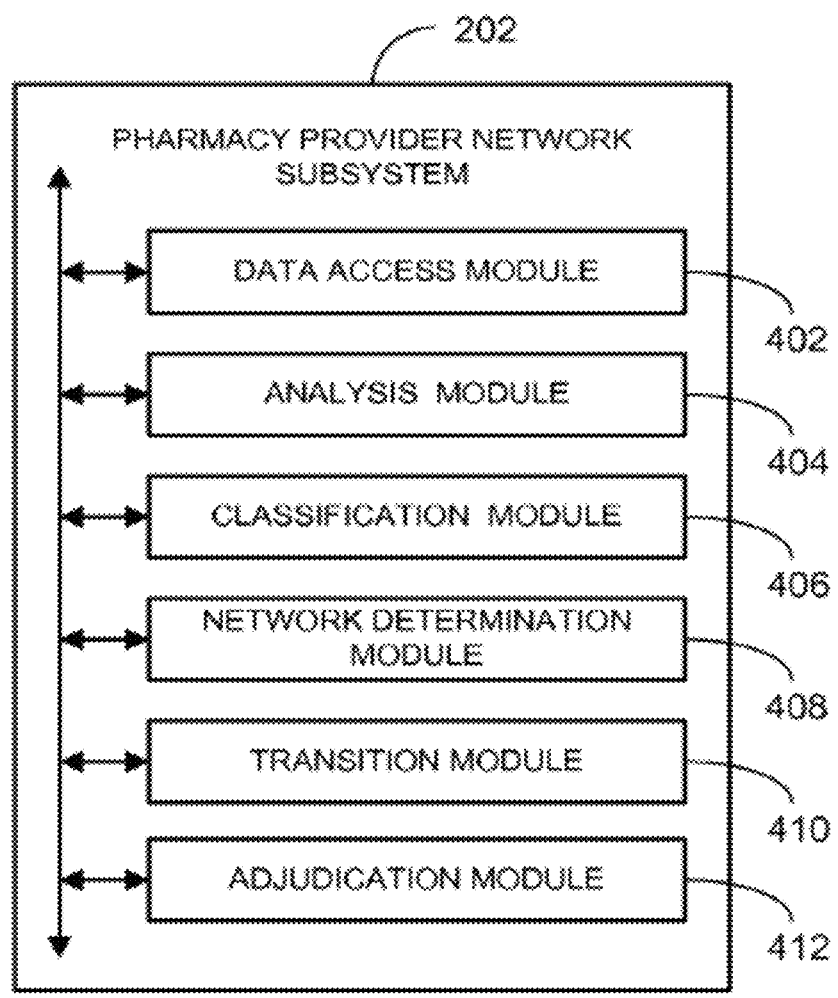
FIG. 4 is a block diagram of an example separate pharmacy provider network subsystem that may be deployed within the pharmacy device of FIG. 2 and/or the pharmacy benefit manager device of FIG. 3, according to an example embodiment.

FIG. 4 illustrates an example pharmacy provider network subsystem 202 that may be deployed in the pharmacy device 102, the pharmacy benefit manager device 108, or otherwise deployed in another system. One or more modules are communicatively coupled and included in the pharmacy provider network subsystem 202 to enable association of a prescribed drug with the appropriate pharmacy provider network. The modules of the pharmacy provider network subsystem 202 that may be included are a data access module 402, an analysis module 404, a classification module, 406, a network determination module 408, a transition module 410, and an adjudication module 412. Other modules may also be included.

In some embodiments, the modules of the pharmacy provider network subsystem 202 may be distributed so that some of the modules are deployed in pharmacy device 102 and some modules are deployed in the pharmacy benefit manager device 108. One, or more than one, of the module of the pharmacy provider network subsystem 202 may be deployed in another device. In one embodiment, the modules are deployed in memory and executed by a processor coupled to the memory. The functionality contained within the modules 402-412 may be combined into a lesser number of modules, further divided among a greater number of modules, or redistributed among existing modules. Other configurations including the functionality of the modules 402-412 may be used.

In some embodiments, the data access module 402 may access claims adjudication data of a member. Claims adjudication data may be associated with each pharmacy claim that is submitted for prescriptions of a member. For example, when a member of a drug benefit program attempts to fill a prescription, the pharmacy at which the member attempts to fill the prescription may transmit various information to the PBM (e.g., between pharmacy device 102 and pharmacy benefit manager device 108) for adjudication of the claim for the prescription. The claims adjudication information may include, for example, an identification of the member for whom the claim is being submitted, and identification of the medication and dosage being prescribed, an identification of the prescribing healthcare professions, etc. As generally discussed above, the PBM may utilize the claim information to determine eligibility and coverage for the prescription, conduct drug utilization review, determine reimbursement rate to the pharmacy, and the like. In an embodiment, the claim information may be the pharmacy claim itself, additional/alternative information, or both. The claims adjudication data for a member may include various additional information and the PBM may perform various additional operations and/or reviews as part of the claim adjudication process.

In some embodiments, claims adjudication data may be accessed by the data access module 402 at the time when a request to fill a prescription is made at a pharmacy by a member. For example, when the member attempts to fill a prescription the member may submit the prescription to the pharmacist (e.g., by either physically submitting a written prescription and/or by directing a prescribing healthcare profession to transmit an electronic prescription to the pharmacy or to the pharmacist). In such an instance, a device operator of the pharmacy device 102 submits an adjudication request to the PBM relative to the prescription. In an embodiment, the adjudication request may include the pharmacy claim itself, submitted to the PBM by the pharmacy. For example, the device operator of the pharmacy device 102 may enter the claims adjudication data (or a portion of the claims adjudication information) into pharmacy device (e.g., via manual entry, scanning a written prescription, or transmitting an electronic prescription to the pharmacy device 102) into and/or via the pharmacy device 102. In such an embodiment, the data access module 402 may access the claims adjudication data (and/or a portion of the claims adjudication data) based on a received adjudication request (e.g., which may include claims adjudication data entered into and/or via the pharmacy device 102) including receiving the entered claims adjudication data.

In some embodiments, the data access module 402 may access claims adjudication data (e.g., which may be included as part of the prescription data 118, in some embodiments) from the database 110. In some embodiments, the data access module 402 may access claims adjudication data by accessing the member data 112 from the database 110, and/or by receiving the claims adjudication data (which may include receiving the member data 112) from another device. Receiving the member data 112 may include, for example receiving the member data 112 through the network 104 form the pharmacy device, the pharmacy benefit manager device 108, or from a different device. In some embodiments, the data access module 402 may access claims adjudication data by receiving claims data entered into, or via, the pharmacy device, and by accessing the member data 112 included within the database 110.

In some embodiments, the data access module 402 may access the claims adjudication data in response to a request to adjudicate a claim on behalf of a member of a drug benefit program. For example, when the member attempts to fill a prescription at a pharmacy, the pharmacy may transmit claims adjudication data (e.g., information that may be used as part of the claims adjudication process) to the PBM. In response to the claims adjudication data being transmitted to the PBM, the data access module 402 may access claims adjudication data associated with the member attempting to fill the prescription. In some embodiments, the data access module 402 may access all claims adjudication data associated with the member, for example, which may include claims adjudication data associated with the prescription the member is attempting to fill as well as claims adjudication data associated with prescriptions that the member has previously filled. In some embodiments, the data access module 402 may access all claims adjudication data associated with the prescription that the member is attempting to fill and/or associated with the prescription that the member is attempting to fill and associated with previous prescriptions for the same drug that have been filled by the member. In some embodiments, the data access module 402 may access all claims adjudication data associated with the member relative to the pharmacy at which the member is attempting to fill the prescription. The pharmacy may include a retail pharmacy location or a mail-order pharmacy. In some embodiments, the data access module 402 may access various combinations of the above claims adjudication data.

In some embodiments, the analysis module 404, may analyze the claim adjudication data of a member to identify a prescribed drug associated with the member. For example, the analysis module 404 may parse the claims adjudication data to determine the drug associated with one, or multiple, pharmacy claims that have been submitted for adjudication by the PBM on behalf of a member. That is, whenever a pharmacy claim is submitted by a pharmacy to the PBM for adjudication, the pharmacy claim includes an identification of the drug. The identification of the drug may be included as a component of the claims adjudication data (e.g., which may be accessed by the data access module 402). The analysis module 404 may analyze the claim adjudication data accessed by the data access module 402 and may determine the drug associated with the member and at least one claim adjudication on behalf of the member.

As generally discussed above, the claim adjudication data accessed by the data access module 402 may include claim adjudication data for a prescription that the member is attempting to fill, claim adjudication data for prescriptions that the member had previously filled, and both the prescription that the member is attempting to fill and prescriptions that the member had previously filled. Accordingly, in some embodiments, the analysis module 404 may identify the drug of a prescription the member is attempting to fill, the drug of prescriptions that the member has previously filled, and/or both the drug of a prescription the member is attempting to fill and drugs of prescriptions that the member has previously filled. In some embodiments, in addition to identifying drugs associated with one, or more than one, prescriptions that the member is attempting to fill or has previously filled, the analysis module 404 may determine the number of times that the member has filled prescriptions for the various drugs. In some embodiments, the analysis module 404 may also determine the dates on which the member filled prescriptions for the various drugs.

In an example embodiment, the analysis module 404 may identify a prescribed drug that a member is attempting to fill, and may generate a message to be transmitted to the member that the member has to fill the identified drug within either the acute medication pharmacy provider network or the maintenance medication pharmacy provider network.

In some embodiments, a classification module 406 may classify identified prescribed drug associated with a member as being either an acute medication or as being a maintenance. For example, the analysis module 404 may identify one, or several, prescriptions associated with a member of a drug benefit program (e.g., based on claims adjudication data accesses by the access module 402). The classification module 406 may classify one, or more than one, of the prescriptions associated with the member as being an acute medication or as being a maintenance medication. By way of illustrative example, three prescribed drugs may be associated with a member. The member may have received prescriptions for each of the three drugs from a prescribing healthcare professional (e.g., which prescriptions may have been received by one or more of the pharmacy device 102 and the pharmacy benefit manager device 106, either via user entry of prescription data, scanning of a prescription, or transmission of an electronic prescription from prescriber device 120), and/or the member may have filled or attempted to fill each of the three prescriptions at a pharmacy (e.g., which may have submitted associated claims to the PBM for each prescription). One of the three prescribed drugs may be an antibiotic that was newly prescribed by a healthcare professional. The classification module 406 may determine that the antibiotic is an acute medication. The other two prescribed drugs associated with the member may be a heart medication and a diabetes medication. The classification module 406 may classify each of the heart medication and the diabetes medication as maintenance medications.

In an embodiment, the classification module 406 may classify prescriptions associated with the member based on one, or more than one, classification rules. The one, or more than one, classification rules may be based on, for example, a drug type or drug category, the specific prescribed drug, on a number of refills/duration of treatment specified by the prescription, or the like. As such, the classification rules may be based on attributes of the prescribed drugs (e.g., specific drug, drug type, drug category, or the like), and/or may be based on attributes associated with a course of treatment or administration of the drugs (e.g., the duration of treatment, number of refills anticipated and/or number of fills actually requested for the prescription or drug, which may span multiple separate prescriptions).

In some embodiments, the classification rules may be based on whether the prescription indicates a number of refills during a specified time period, a number a refills requested by the member (e.g., within a specified time period), or the like. For example, a classification rule may specify that three or more refills of a drug and/or prescription is classified as a maintenance medication. In a situation in which a prescription indicates that six refills of a prescription are available (e.g., three or more refills), the classification module 406 may classify the prescription and/or the drug as being a maintenance medication for the member as the number of refills may exceed an acute medication threshold number of fills (or fill requests). Similarly, if a member attempts to refill a prescription for a drug for a third time (or attempts to get a fill of a drug for which the member has received two fills of the same drug within a specified period of time), the classification module 406 may classify the drug as a maintenance medication. As such, the classification module 406 may classify the drug as a maintenance medication when a first fill of a prescription is requested (e.g., if the prescription indicates that three or more fills are available), or may classify the drug as a maintenance medication when a member requests a third or subsequent refill of the medication. With respect to the latter example, the classification module 406 may initially classify a drug as an acute medication (e.g., when the first and second fills of the prescription are requested by the member). Further, upon the member requesting a third fill of the prescription, the classification module 406 may classify the drug as a maintenance drug.

While the foregoing example has related to the classification of a drug as being a maintenance medication if three, or a greater number, of refills are requested, this is intended only for the purpose of illustration, as the threshold number of refills may vary for classifying a drug as a maintenance medication, and/or classification rules unrelated to the number of fills or refills of a prescription may be utilized. Additionally, in some embodiments, some drugs may be classified as a maintenance drug based on the specific drug, the drug category, the drug type, or the like. In some such embodiments, drugs classified as maintenance medications may be classified as maintenance medications for all members of a drug benefit program. In some embodiments (for example, including embodiments in which a drug may be classified based on a number of fills), a drug may be classified as a maintenance medication with respect to only a specific member of a drug benefit program. In such an embodiment, the classification of drugs as an acute medication or a maintenance medication may occur on a member-by-member basis.

In some embodiments, the classification module 406 may classify a prescribed drug associated with a pharmacy claim of an adjudication request as an acute medication or a maintenance medication. In some embodiments, the classification module 406 may access one or more other data sources, such as a web server, database or other storage device to access information used to classify identified prescribed drug.

In some embodiments, the network determination module 408 may use the classification provided by the classification module 406 to determine or select which pharmacy provider network to associate with the classified prescribed drug. For example, if the classification module 406 classifies the drug as an acute medication, the network determination module 408 may associate the prescribed drug for the member with an acute medication pharmacy network. In an embodiment in which the classification module 406 classifies the drug as a maintenance medication, the network determination module 408 may associated the prescribed drug for the member with a maintenance medication pharmacy network.

In some embodiments, the network determination module 408 may determine if a pharmacy at which a fill of the prescription drug is requested is a pharmacy associated with an acute medication pharmacy provider network, or if the pharmacy at which the fill of the prescription drug is requested is a pharmacy associated with a maintenance medication pharmacy provider network. In some embodiments, the network determination module may access the acute medication pharmacy network data 114 and/or the maintenance medication pharmacy network data 116 from the database 110. In some embodiments, accessing the acute and/or maintenance medication pharmacy network data 114/116 may include receiving the data from the database 110. Receiving the data 114, 116 from the database may include receiving the data 114, 116 over the network 104 from the pharmacy device, the member device 106, the pharmacy benefit manager device 108, or from another device. The network determination module 408 may compare the pharmacy at which the request for the fill of the prescription is made to the pharmacies included in the acute/maintenance pharmacy network data 114/116.

In some embodiments, the transition module 410 may be used to transition a prescribed drug associated with a member from one pharmacy provider network to a different pharmacy provider network. For example, the transition module 410 may transition a prescribed drug associated with a member from an acute medication pharmacy provider network to a maintenance medication pharmacy provider network. Transitioning a prescribed drug associated with a member from an acute medication pharmacy provider network to a maintenance medication pharmacy provider network may include associating different member benefits for fills of the prescribed drug at pharmacies within the acute medication pharmacy provider network than the benefits associated with fills of the prescribed drug at pharmacies within maintenance pharmacy provider network. The different member benefits may be the co-pay required by the member for fills of the prescription, coverage eligibility of fills of the prescription by the member, or other member benefits provided for fills of the prescription under the drug benefit program. The difference in member benefits provided for fills of the prescription at acute medication pharmacy provider network pharmacies as compared to member benefits provided for fills of the prescription at a maintenance medication pharmacy provider network pharmacy may motivate the member to seek fills at pharmacies within one network rather than the other, e.g., by requiring a higher co-pay, or denying coverage eligibility for fills of the prescription at pharmacies of one provider network, denying coverage at one provider network, or the like.

For example, a member receive a prescription (e.g., from a prescribing healthcare professions) and may fill the prescription at a pharmacy included within an acute medication pharmacy provider network. The prescription may initially be classified as an acute medication by the classification module 406 (e.g., based on one or more classification rules). As such, the network determination module 408 may associate the prescription with the acute medication pharmacy provider network, and the transition module 410 may associate a first set of member benefits for fills of the prescription by the member at the pharmacy within the acute medication pharmacy provider network. Subsequently (e.g., in response to the member seeking additional fills of the prescription and/or fills of subsequent prescription for the same drug within a specified time period or the like), the classification module 406 may classify the prescription for the drug as a maintenance medication (e.g., based on one, or more than one, classification rules).

In response to the classification module 406 classifying the prescription as a maintenance medication, the network determination module 408 may associate the prescription for the drug with a maintenance pharmacy provider network. In response to the network determination module 408 associating the prescription drug with a maintenance pharmacy provider network, the transition module 410 may associated a modified set of benefits with the member for fills of the prescription at pharmacies within an acute medication pharmacy provider network. For example, the transition module 410 may associate a first set of benefits with the member for fills of the prescription at pharmacies within an acute medication pharmacy provider network. The transition module 410 may further associated a second set of benefits with the member for fills of the prescription at pharmacies within a maintenance medication pharmacy provider network.

For example, first set of benefits may include a denial of coverage (or an elevated co-pay, or other benefits) for fills of the prescription at pharmacies within the acute medication pharmacy provider network, and the second set of benefits may include full covers (or a lower co-payor other benefits) for fills of the prescription at pharmacies within the maintenance medication pharmacy provider network. Accordingly, the difference between the first set of benefits and the second set of benefits may motivate the member to seek fills of the medication at pharmacies within the maintenance medication pharmacy provider network. In some embodiments, the transition module 410 may transmit a warning to the member attendant to associating the first set of benefits with fills of the prescription at pharmacies within the acute medication pharmacy provider network. For example, the member may be permitted a single additional fill (and/or partial fill) of the prescription before the first set of benefits are associated with fills of the prescription at pharmacies within the acute medication pharmacy provider network. Such a warning may be transmitted, for example, to the pharmacy device 102, wherein the warning may be conveyed to the member by the operator of the pharmacy device. As such, the member may not experience a lapse in the prescription while the member seeks out fills of the prescription at a pharmacy within a maintenance medication pharmacy provider network consistent with the second set of member benefits.

In some embodiments, multiple pharmacy provider networks may be available for members. For example, actions associated with filling a prescription for an acute medication may be different than actions associated with filling a maintenance medication. In either the acute or the maintenance medication pharmacy provider networks, there may be different costs associated with the different networks. For example, costs may be influenced by agreements between the PBM and pharmacies within the maintenance medication pharmacy provider networks and between the PBM and pharmacies within the acute medication pharmacy provider networks. For example, agreements between the PBM and pharmacies within the maintenance medication pharmacy provider network may provide for a lower reimbursement rate (of the pharmacy by the PBM) for maintenance drugs dispensed for member by the pharmacies within the maintenance medication pharmacy provider network than for maintenance drugs dispensed for members by pharmacies within the acute medication pharmacy provider network. For example, different agreements may result from different fulfillment costs borne by the pharmacies in fulfilling member prescriptions at pharmacies within the maintenance medication pharmacy provider network as compared to pharmacies within the acute medication pharmacy provider network.

The adjudication module 414 may adjudicate the claim received from the pharmacy by the adjudication request module. For example, the pharmacy claim for the prescription fulfilled for the member may be adjudicated, which may in some embodiments include operations such as conducting a DUR relative to the prescription, determining member coverage, etc. In some embodiments, the adjudication module may adjudicate the pharmacy claim for the prescribed drug based on the claim and the pharmacy provider network in which the pharmacy submitting the claim is included. In an embodiment in which the prescription drug may be classified as a maintenance medication and the pharmacy may be determined to be included within an acute medication pharmacy provider network, the claim may be adjudicated using the first set of member benefits (e.g., the set of member benefits for prescriptions for maintenance medications filled at pharmacies included within acute medication pharmacy provider networks). Upon successful adjudication of the claim by the adjudication module, the PBM may approve the claim. In some embodiments, the adjudication module may also transmit an adjudication response based on the adjudication of the claim. In some embodiments, the warning transmitted by the transition module 410 may be transmitted with, and/or as part of, the adjudication response.

The adjudication of a claim, or the adjudication response, may involve automatically filling the corresponding prescription (e.g., without further operator intervention) or automatically sending instructions to direct a system or person to fill the corresponding prescription. The adjudication module can communicate the adjudication response to a packaging subsystem that can fill the corresponding prescription.

Figure 5:
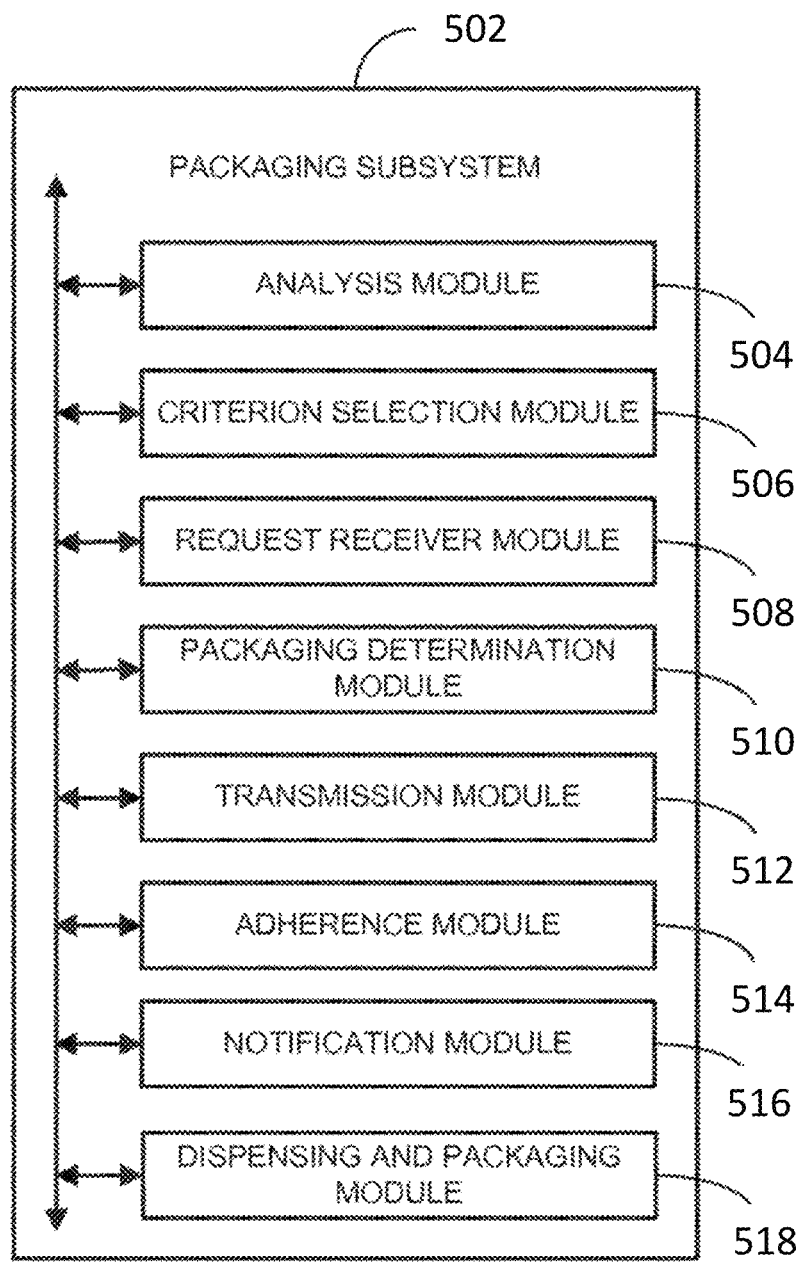
FIG. 5 illustrates an example packaging subsystem that may be deployed in the pharmacy device, the benefit manager device, or otherwise deployed in another system.

FIG. 5 illustrates an example packaging subsystem 502 that may be deployed in the pharmacy device 102, the benefit manager device 108, or otherwise deployed in another system. One or more modules are communicatively coupled and included in the packaging subsystem 502 to package prescription drugs. The modules of the packaging subsystem 502 that may be included are an analysis module 504, a criterion selection module 506, a request receiver module 508, a packaging determination module 510, a transmission module 512, an adherence module 514, a notification module 516, and a dispensing and packaging module 518. Other modules may also be included.

In some embodiments, the modules of the packaging subsystem 502 may be distributed so that some of the modules are deployed in the pharmacy device 102 and some modules are deployed in the benefit manager device 108. In one embodiment, the modules are deployed in memory and executed by a processor or more than one processor coupled to the memory. The functionality contained within the modules 504, 506, 508, 510, 512, 514, 516, 518 may be combined into a lesser number of modules, further divided among a greater number of modules, or redistributed among existing modules. Other configurations including the functionality of the modules 504, 506, 508, 510, 512, 514, 516, 518 may be used.

In some embodiments, the analysis module 504 analyzes prescription drugs that have been prescribed to a patient population and/or taken by the patient population and identifies one, or more than one, prescription drugs among the prescribed and/or taken prescription drugs as being a maintenance drug that could be fulfilled through prescription bottle fulfillment or blister packaging fulfillment. The patient population may include all members of a single client, a subset of all members of a single client, al, or a subset of members of multiple clients, or the like. For example, certain types of drugs may be commonly taken by the population and are in the form of a pill or other type of drug that could be packaged in at least blister packaging. Data reflecting the prescription drugs prescribed to the patient population may come from data received from prescribers, from an electronic prescribing network (e.g., directly from the network or through a device associated with an entity responsible for electronic prescribing network), PBMs, or otherwise. Data reflecting the prescription drugs taken by the patient population may come from claims data, claims data received from another source, or otherwise.

The analysis module 504 may thereby identify one, or more than one, type of drugs for the patient population as being candidates for selection by the criterion selection module 506. For example, a prescription drug that is taken through an inhaler may be identified as not being a candidate for selection because of unavailability through prescription bottle fulfillment or blister packaging fulfillment (e.g., but rather as being available for unit-of-use fulfillment), while a prescription drug taken in tablet form may be identified as being a candidate for selection as being available through prescription bottle fulfillment or blister packaging fulfillment.

In some embodiments, the analysis module 504 uses drug data (as stored in the database 110 and/or in another database) in identifying candidate drugs for selection. For example, the drug data may include packaging information regarding the prescription drugs. In some embodiments, the pharmacy device 102 analyzes or accesses its drug inventory including, in some embodiments, packaging information to identify candidate drugs for selection.

The analysis of the prescription drugs to identify prescription drugs as being a maintenance drug may be made by the analysis module 504 in a number of different methods. In some embodiments, a prescription drug is identified as a maintenance medication or drug (or as commonly used as a maintenance medication or drug) in the drug data. Such identification may be made by the manufacturer of the prescription drug, a health care provider associated with the prescription drug, a PBM or other benefit manager associated with the prescription drug, a governmental organization, or a different entity.

In some embodiments, a PBM may analyze the claim data of one or a number of members to identify prescription drugs as maintenance medications. For example, claims that reflect continuing usage by members over a period of time (e.g., multiple refills) may be identified as maintenance drugs, while claims that reflect acute usage by members (e.g., one-time usage during a certain time period) may be identified as not being a maintenance medication.

The criterion selection module 506 selects blister packaging criterion used for some or all of the drugs (e.g., in one class, or more than one class of drugs) based on analysis performed by the analysis module 504. In general, the blister packaging criterion establishes one, or more than, criterion for determining whether a prescription drug should be filled with blister packaging instead of other packaging that may be available (e.g., a prescription bottle of a particular size). The blister packaging criterion may be made in general for a type of prescription drug across an entire patient population, or may be specific to certain patients or groups of patients.

In some embodiments, blister packaging includes a cavity or pocket made from a formable web, usually a thermoformed plastic. In some embodiments, blister packaging includes a backing of paperboard or a lidding seal of aluminum foil or plastic. Non-blister packaging generally includes other types of prescription drug containers such as bottles in a variety of sizes that are sealed with lids. The type and/or characteristics of packaging available may depend on the pharmacy devices 102 available in the system 100.

In some embodiments, the analysis module 504 reviews a number of commonly used maintenance drugs by the patient population. The number may be a threshold, may be a number designated by a person or entity associated with the creation, deployment, and/or usage of the packaging determination subsystem 502. By way of example, the number and type of drugs may be such as to enable a certain percentage usage across the patient population of blister packaging on at least one prescription drug that is likely to be taken by a member in the patient population. In some embodiments, not all prescription drugs taken by a patient or member are ultimately selected for blister packaging. Rather, a subset of prescription drugs are selected while member adherence improves for all prescription drugs (including those not in blister packaging).

In some embodiments, the analysis module 504 utilizes one, or more than one, models and/or classifiers for use in analysis and/or identification of prescription drugs as being a common maintenance drug. The analysis module 504 may include models and/or classifiers such as group method of data handling, naive bayes, k-nearest neighbor algorithm, majority classifier, support vector machine, logistic regression, uplift modeling, or the like. Such functionality may enable a more sophisticated selection of prescription drugs to be packaged in blister packaging, and/or may further individualize the selection of one, or more than one, prescription drug to be packaged in blister packaging for a particular patient.

The analysis module 504 determines that a person (e.g., a member of a pharmacy benefit plan and/or a patient of a pharmacy) has had prescription drugs that have previously been filled. The drugs may have been filled through an entity making the determination through the analysis module 504, or through another entity (e.g., by a retail pharmacy or a mail order pharmacy). The determination relative to the member may be made through analysis of the claims data associated with the member or otherwise.

In some embodiments, the adherence module 514 may determine the adherence of the member. When the member's adherence is below a certain threshold, the analysis performed by the analysis module 504 may be made to determine whether the member is an appropriate candidate to receive (or continue to receive) blister packaging for one, or more than one, type of prescription drug. When the member's adherence is above a certain threshold, the member may not be a candidate to receive blister packaging (e.g., for adherence reasons) based on the analysis performed by the analysis module 504.

The request receiver module 508 receives a request for a prescription drug prescribed to the member. In some embodiments, the request is an adjudication request associated with a fulfillment request to fill the prescription drug. In general, the adjudication request reflects that the member is seeking to have a prescription drug filled as either a new prescription or renewal. In some embodiments, the request is a fulfillment request to fill the prescription drug on behalf of the patient.

The packaging determination module 510 determines packaging to use to fill the prescription drug associated with the received request. In some embodiments, the determination of the packaging may be in response to receipt of the request for the prescription drug.

In some embodiments, the packaging determination made by the packaging determination module 510 is based on whether a blister packaging criterion has been met. The blister packaging criterion may identify a single prescription drug or multiple prescription drugs for blister packaging and reflect that a member or patient has had a prescription drug of the same or similar type that has previously been filled. For example, this determination may be on the basis of the patient (e.g., low patient adherence), on the basis of the prescription drug (e.g., commonly available and in a form that can be filled in blister packaging or is available in blister packaging), and the like. By making the determination, the packaging determination module 408 may identify the prescription drug associated with the current request to be filled with blister packaging.

By way of example, the prescription drug may be selected by the packaging determination module 408 among the prescription drugs that have previously been filled on behalf of the member to fill in blister packaging on behalf of the member. A determination may then be made by the packaging determination module 510 that the blister packaging criterion has been met based on selection of the prescription drug to fill in the blister packaging and receipt of the request for the prescription drug.

In some embodiments, the transmission module 512 transmits a blister fill instruction based on receipt of the request and a determination that the blister packaging criterion has been met and/or based on receipt of the adjudication response from the transition module 410. The blister fill instruction may reflect that the pharmacy device 102 is to fill the prescription drug utilizing blister packaging. In some embodiments, an adjudication response includes a blister fill instruction. In other embodiments, the blister fill instruction is sent separate from the adjudication response.

As described above, adherence may be determined by the adherence module 514 to determine whether a member should receive blister packaging. In some embodiments, however, the adherence module 514 may determine adherence before and after a prescription drug is provided in blister packaging to determine a difference in adherence for the prescription drug provided in blister packaging and other prescription drugs that have not been provided to the member in blister packaging. Thus, the adherence module 514 may operate in conjunction with the analysis module 504 and/or the criterion selection module 506 to determine whether the member should receive the prescription drug in blister packaging as opposed to a fill in a prescription bottle.

By way of example, the adherence module 514 measures prior prescription drug adherence of the member prior to transmission of an adjudication response and measures after prescription drug adherence of the member for a period of time after transmission of the blister fill instruction, the period of time including at least one time period during which the prescription drug was prescribed to be taken by the member prior to prescription drug refill, and compares the prior prescription drug adherence and the after prescription drug adherence. The notification module 516 generates a notification based on comparison of the prior prescription drug adherence and the after prescription drug adherence. In some embodiments, the notification reflects that the after prescription drug adherence of the member is greater than the prior prescription drug adherence for both the prescription drug in blister packaging and any other drugs prescribed to be taken by the member that are not in blister packaging. As a result of the difference in adherence, the benefit manager, or another party, may receive a greater amount of reimbursement directly or indirectly from the client.

Not every prescription drug prescribed to the patient may be packaged in blister packaging. In some embodiments, the request receiver module 508 receives an additional request for an additional prescription drug prescribed for the member and the packaging determination module 510 determines that the blister packaging criterion has not been met based on a drug type of the prescription drug. As such, the packager of the prescription drugs (or the client, benefit manager, etc.) may not incur increased packaging cost for every prescription drug, but merely a subset of one or more than one prescription drug fulfilled for the member. The transmission module 512 may therefore transmits an additional response to the additional request. In some embodiments, the additional request reflects that the pharmacy is to fill the prescription drug accordance to standard fulfillment instructions.

The dispensing and packaging module 518 dispenses and packs a prescription drug into packaging (e.g., the prescription container). In some embodiments, the dispensing and packaging module 518 dispenses and packs the prescription drug into blister packaging based on receipt of the request for the prescription drug, receipt of the adjudication response, and a determination that the blister packaging criterion has been met. In some embodiments, the dispensing and packaging module 518 dispenses and packs the prescription drug into based on receipt of the blister fill instruction. The blister packaging may be performed by the pharmacy device 102 (e.g., at or before the time of fill), by a drug manufacture of the prescription drug, or otherwise. Once packed, the prescription drug may be provided to the member through mail order, in person (e.g., at a retail pharmacy), or otherwise.

Figure 6:
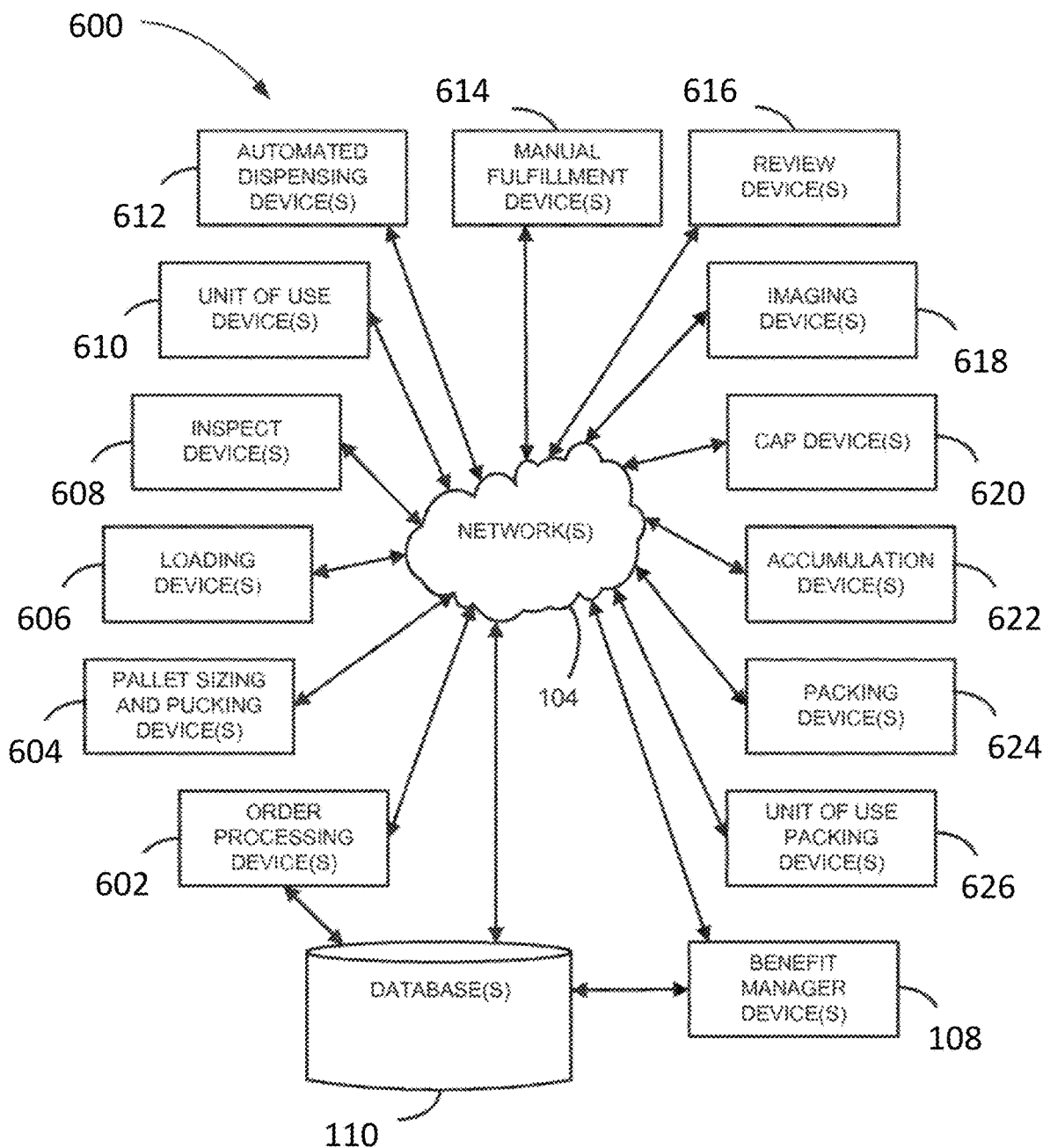
FIG. 6 is a block diagram of an example filling system according to an example embodiment.

FIG. 6 is a block diagram of an example filling system 600, according to an example embodiment. While the system 600 is generally described as being deployed in a high volume pharmacy (e.g., a mail order pharmacy, a direct delivery pharmacy, and the like), the system 600 may otherwise be deployed. Some embodiments of a high volume pharmacy are described in U.S. Pat. No. 9,697,335; application Ser. No. 14/807,596; titled "Methods and systems for automated pharmaceutical dispensing," which is hereby incorporated by reference. In some embodiments, the system 600 includes the system 100 and/or the subsystem 502. The pharmacy device 102 of FIG. 1 may be reflected as devices 602-626 in the system 600.

The system 600 may include an order processing device 602 in communication with the benefit manager device 108 over the network 104. The order processing device 602 may receive information about prescriptions being filled at a pharmacy in which the order processing device 602 is deployed. The order processing device 602 may track a prescription order as the order is fulfilled. A prescription order may include one or more than one prescription to be filled by the pharmacy. The order processing device 602 may make pharmacy routing decisions and/or order consolidation decisions for a prescription order. The pharmacy routing decisions include what device or devices in the pharmacy are responsible for filling at least a portion of the prescription order, where the order consolidation decisions include whether portions of a prescription order or multiple prescription orders should be shipped together for a patient or a patient family. The order processing device 602 may operate in combination with the benefit manager device 108. In some embodiments, the order processing device 602 includes the packaging subsystem 502 and one or more than one of the modules of the packaging subsystem 502.

The order processing device 602 and/or the benefit manager device 108 may be in communication directly (e.g., through local storage) and/or through the network 104 (e.g., in a cloud configuration or software as a service) with the database 110 (e.g., as may be retained in memory or otherwise). The database 110 may store order data, member data, claims data, drug data, prescription data, and/or plan sponsor data. Other data may be stored in the database 110, as described herein.

The order data may include data related to the order of prescriptions including the type (e.g., drug name and strength) and quantity of each prescription in a prescription order. The order data may also include data used for completion of the prescription, such as prescription materials. In general, prescription materials are a type of order materials that include an electronic copy of information regarding the prescription drug for inclusion with or otherwise in conjunction with the fulfilled prescription. The prescription materials may include electronic information regarding drug interaction warnings, recommended usage, possible side effects, expiration date, date of prescribing, or the like.

The prescription data may include information regarding prescriptions that may be issued by prescribers on behalf of patients, who may be members of the drug benefit plan, for example to be filled by a pharmacy. Examples of the prescription data include patient names, medication or treatment (such as lab tests), dosing information, and the like. The prescriptions may be electronic prescriptions, paper prescriptions that have been scanned, or otherwise. In some embodiments, the dosing information reflects a frequency of use (e.g., once a day, twice a day, before each meal, etc.) and a duration of use (e.g., a few days, a week, a few weeks, a month, etc.).

The system 600 may include a pallet sizing and pucking device 604, a loading device 606, an inspect device 608, a unit of use device 610, an automated dispensing device 612, a manual fulfillment device 614, a review device 616, an imaging device 618, a cap device 620, an accumulation device 622, a packing device 624, and/or a unit of use packing device 626. The system 600 may also include additional devices. The order processing device 602 may direct at least some of the operations of these devices 604-626. In some embodiments, operations performed by one of these devices 604-626 may be performed sequentially, or in parallel with the operations of another device as may be coordinated by the order processing device 602. The order processing device 602 may receive the adjudication response described above and control (e.g., direct through generation and communication of signals to) the devices 604-626.

In some embodiments, the system 600 may transport prescription drug containers by use of pallets. The pallet sizing and pucking device 604 may configure (e.g., arrange or otherwise move) pucks in a pallet. A pallet may be a transport structure for a number of prescription containers, and may include a number of cavities. A puck may be placed in one or more than one of the cavities in a pallet by the pallet sizing and pucking device 604. A puck may include a receptacle sized and shaped to receive a prescription container. Such containers may be supported by the pucks during carriage in the pallet. Different pucks may have differently sized and shaped receptacles to accommodate containers of differing sizes, as may be appropriate for different prescriptions.

The arrangement of pucks in a pallet may be determined by the order processing device 602 based on prescriptions which the order processing device 602 decides to launch based on the adjudication response. For example, responsive to receiving the adjudication response, the order processing device 602 can decide to launch one or more pallets containing the medication(s) identified in or otherwise associated with the adjudication response. In general, prescription orders in the database 110 reside in one or more than one queues, and are generally launched in a first-in-first-out order. The order processing device 602, however, may use logic and a variety of factors (e.g., the adjudication response) to determine when and how prescriptions are to be launched. For example, some non-limiting factors which may alter the first-in-first-out order of launching prescriptions in a pharmacy include the age of the order, whether the order required an outreach to a physician or some other intervention, whether there are any performance guarantees with plan sponsors or members, the available inventory of a given pharmaceutical in view of existing prescriptions already launched which will require that pharmaceutical, the zip code to which the order will be shipped, the workload and volume of various parts of the pharmacy, receipt of the adjudication response, whether valid paperwork for the order has been received, and/or similar orders for the same pharmaceutical that are already to be launched. The logic may be implanted directly in the pallet sizing and pucking device 604, in the order processing device 602, in both devices 602, 604, or otherwise. Once a prescription is set to be launched, a puck suitable for the appropriate size of container for that prescription may be positioned in a pallet by a robotic arm or pickers. The pallet sizing and pucking device 604 may launch a pallet once pucks have been configured in the pallet.

The loading device 606 may load prescription containers into the pucks on a pallet by a robotic arm, pick and place mechanism, or the like. In one embodiment, the loading device 606 has robotic arms or pickers to grasp a prescription container and move it to and from a pallet. The loading device 606 may also print a label which is appropriate for a container that is to be loaded onto the pallet, and apply the label to the container. The pallet may be located on a conveyor assembly during these operations.

The inspect device 608 may verify that containers in a pallet are correctly labeled and in the correct spot on the pallet. The inspect device 608 may scan the label on one or more than one container on the pallet. Labels of containers may be scanned or imaged in full or in part. Such imaging may occur after the container has been lifted out of its puck by a robotic arm, picker, or the like, or may be otherwise scanned or imaged while retained in the puck.

The unit of use device 610 may temporarily store, monitor, label and/or dispense unit of use products. In general, unit of use products are prescription drug products that may be delivered to a patient or member without being repackaged at the pharmacy. These products may include pills in a container, pills in a blister pack, inhalers, and the like.

The automated dispensing device 612 may include one or more than one devices that dispense prescription drugs or pharmaceuticals into prescription containers such as prescription bottles and blister packs in accordance with one or multiple prescription orders. The automated dispensing device 612 dispenses a number of prescription drugs or pharmaceuticals according to the output from various methodology as described herein. Such methodology can include whether a pharmacy associated with the claims adjudication data is included within the pharmacy provider network type that is associated with the prescribed drug; adjudicating a pharmacy claim for the prescribed drug through the pharmacy, the claims adjudication data, and determination of whether the pharmacy is included within the pharmacy provider network type; communicating an adjudication response indicative of the pharmacy claim that is adjudicated to an order processing device at a pharmacy filling system via a communication network; or combinations thereof. In general, the automated dispensing device 612 may include mechanical and electronic components with, in some embodiments, software and/or logic to facilitate pharmaceutical dispensing that would otherwise be performed in a manual fashion by a pharmacist and/or pharmacist technician. For example, the automated dispensing device 612 may include blister pack machines that dispense and pack drugs into a blister pack and/or a pill dispensing machines that that dispense and pack drugs into a prescription bottle.

The manual fulfillment device 614 may provide for manual fulfillment of prescriptions. For example, the manual fulfillment device 614 may receive or obtain a container and enable fulfillment of the container by a pharmacist or pharmacy technician. In some embodiments, the manual fulfillment device 614 provides the filled container to another device in the system 600 to be joined with other containers in a prescription order for a patient or member. In general, a manual fulfillment may include operations at least partially performed by a pharmacist or pharmacy technician. For example, a person may retrieve a supply of the prescribed drug, may make an observation, may count out a prescribed quantity of drugs and place them into a prescription container, or the like. Some portions of the manual fulfillment process may be automated by use of a machine. For example, counting of capsules, tablets, or pills may be at least partially automated (e.g., through use of a pill counter).

The review device 616 may process prescription containers to be reviewed by a pharmacist for proper pill count, exception handling, prescription verification, and the like. Fulfilled prescriptions may be manually reviewed and/or verified by a pharmacist, as may be required by state or local law. A pharmacist or other licensed pharmacy person who may dispense certain drugs in compliance with local and/or other laws may operate the review device 616 and visually inspect a prescription container that has been filled with a prescription drug. The pharmacist may review, verify, and/or evaluate drug quantity, drug strength, and/or drug interaction concerns, or otherwise perform pharmacist services. The pharmacist may also handle containers which have been flagged as an exception, such as containers with unreadable labels, containers for which the associated prescription order has been cancelled, containers with defects, and the like.

The imaging device 618 may image containers once they have been filled with pharmaceuticals. The imaging device 618 may measure the fill height of the pharmaceuticals in the container based on the obtained image to determine if the container is filled to the correct height given the type of pharmaceutical and the number of pills in the prescription. Images of the pills in the container may also be obtained to detect the size of the pills themselves and markings thereon.

The cap device 620 may be used to cap certain types of prescription containers such as a prescription bottle. In some embodiments, the cap device 620 may provide a type of cap in accordance with a patient preference (e.g., a preference regarding child resistance), a plan sponsor preference, a prescriber preference, or the like. The cap device 620 may also etch a message into the cap, although this process may be performed by a subsequent device.

The accumulation device 622 accumulates various containers of prescription drugs in a prescription order. The accumulation device 622 may accumulate prescription containers from various areas of the pharmacy. For example, the accumulation device 622 may accumulate prescription containers from the unit of use device 610, the automated dispensing device 612, the manual fulfillment device 614, and the review device 616.

The packing device 624 packages a prescription order in preparation for shipping the order. The packed prescription order may package prescription containers that are of the same dimensions or different (e.g., different prescription bottle sizes, blister packaging and prescription bottle, and the like). The packing device 624 may box or bag the fulfilled prescription order for delivery. The packing device 624 may further place inserts into the box or bag. For example, bulk prescription orders may be shipped in a box, while other prescription orders may be shipped in a bag which may be a wrap seal bag. The packing device 624 may label the box or bag with the address and a recipient's name.

The packing device 624 may sort the box or bag for mailing in an efficient manner (e.g., sort by delivery address). The packing device 624 may include ice or temperature sensitive processing for prescriptions which are to be kept within a temperature range during shipping in order to retain efficacy or otherwise. The ultimate package may then be shipped through postal mail, through a mail order delivery service that ships via group and/or air (e.g., UPS, FedEx, or DHL), through delivery service, through a locker box at a shipping site (e.g., Amazon locker or a PO Box), or otherwise. The unit of use packing device 626 packages a unit of use prescription order in preparation for shipping the order. The unit of use packing device 626 may include manual scanning of containers to be bagged for shipping to verify each container in the order.

A fulfillment gateway system can be provided or used to control and/or coordinate operations of the pharmacy provider network subsystem 202, the packaging subsystem 502, and/or the filling system 600. For example, the gateway system can receive prescription orders, adjudication responses associated with the prescription orders, or the like, and associate the prescription orders with order messages containing information for the packaging subsystem 502 and/or the filling system 600.

Figure 7:
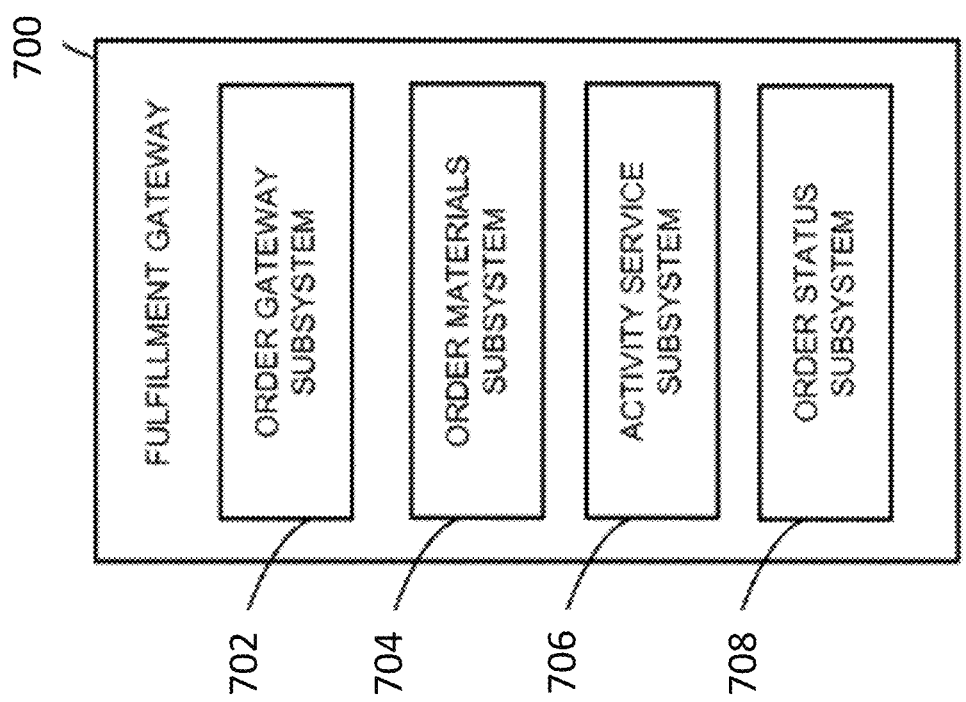
FIG. 7 illustrates one example of a fulfillment gateway system.

FIG. 7 illustrates one example of a fulfillment gateway system 700. The fulfillment gateway system 700 may include an order gateway subsystem 702, an order materials subsystem 704, an activity service subsystem 706, and/or an order status subsystem 708. Other subsystems may also be included. The order gateway subsystem 702 manages communications for the fulfillment gateway system, including coordination of communications to/from the order materials subsystem 704, the activity service subsystem 706, and an order status subsystem 708. The order gateway subsystem 702 also can receive prescription orders and/or the adjudication responses described herein. For example, the order gateway subsystem 702 provides communications for receiving prescription orders from the order processing station and/or the adjudication responses from the pharmacy provider network subsystem 202. The order gateway subsystem 702 also may provide a storage unit for order messages that are assigned or not yet assigned to various fulfillment devices 612, 614.

The order materials subsystem 704 obtains order materials and/or adjudication responses for use at the fulfillment devices 612, 614. The order materials are an electronic record of information needed by the fulfillment devices 612, 614 to implement fulfillment of the prescription according to policies and preferences of patients, clients, and the fulfillment devices 612, 614. Thus, an electronic record can be developed for the fulfillment devices 612, 614, thereby limiting reliance of the fulfillment devices 612, 614 on other devices for information. In some embodiments, order materials and/or adjudication response are stored at the fulfillment devices 612, 614. In other embodiments, order materials and/or adjudication responses are aggregated from the order data by accessing the database 110. The order materials and/or adjudication responses can be included in the order message associated with the prescription order. Order materials and/or adjudication responses may include at least some portions of the patient data, the client data, the pharmacy data, prescription parameters, dispensation preferences and/or prescription materials.

Prescription materials are a type of order materials that include information regarding the prescription drug for inclusion with the fulfilled prescription. The prescription materials may include electronic information regarding drug interaction warnings, recommended usage, possible side effects, etc. for printing and inclusion with the fulfilled prescription for shipping. The order materials subsystem 704 may electronically format the order materials into useable fields. For example, the patient data and/or or the client data may include dispensation preferences such as the inclusion of an invoice with the fulfilled prescription, the inclusion of a return envelope for remitting payment with the fulfilled prescription, the use of a child proof cap, the inclusion of reminders printed on a label, cap or leaflet, the inclusion of consumer survey leaflets, the inclusion of a message encouraging therapy adherence on a label, cap or leaflet, or the like.

The activity service subsystem 706 tracks operations performed by the fulfillment gateway 700 and stores the operations for historical reporting and visibility as activity data. In some embodiments, through the order gateway subsystem 702, the order status subsystem 708 receives order status updates and/or adjudication responses periodically or on a non-periodic basis. The order status subsystem 708 keeps an update on a prescription order as the order progresses through the fulfillment gateway 700 for possible intervention in the fulfillment. The order status subsystem 708 has the capability of instructing that a prescription order be cancelled, paused, or changed based on the adjudication response. Cancelling, pausing, or changing the prescription order may avoid the fulfillment of prescriptions that are no longer needed by the patient or that are denied as a result of the adjudication response, and are therefore of little use. For example, if a patient decides to transfer the prescription to another pharmacy or the adjudication response indicates that the prescription fill request is denied, the order status subsystem 708 can determine the status of the order and send a command to cancel the prescription order via the order gateway subsystem 702 to the fulfillment devices 612, 614. An example of changing the prescription order may be the substitution of a drug in the same class with the previously prescribed drug because of recent formulary changes. Changing the prescription order may include changing prescription parameters such as the address of the patient.

Figure 8:
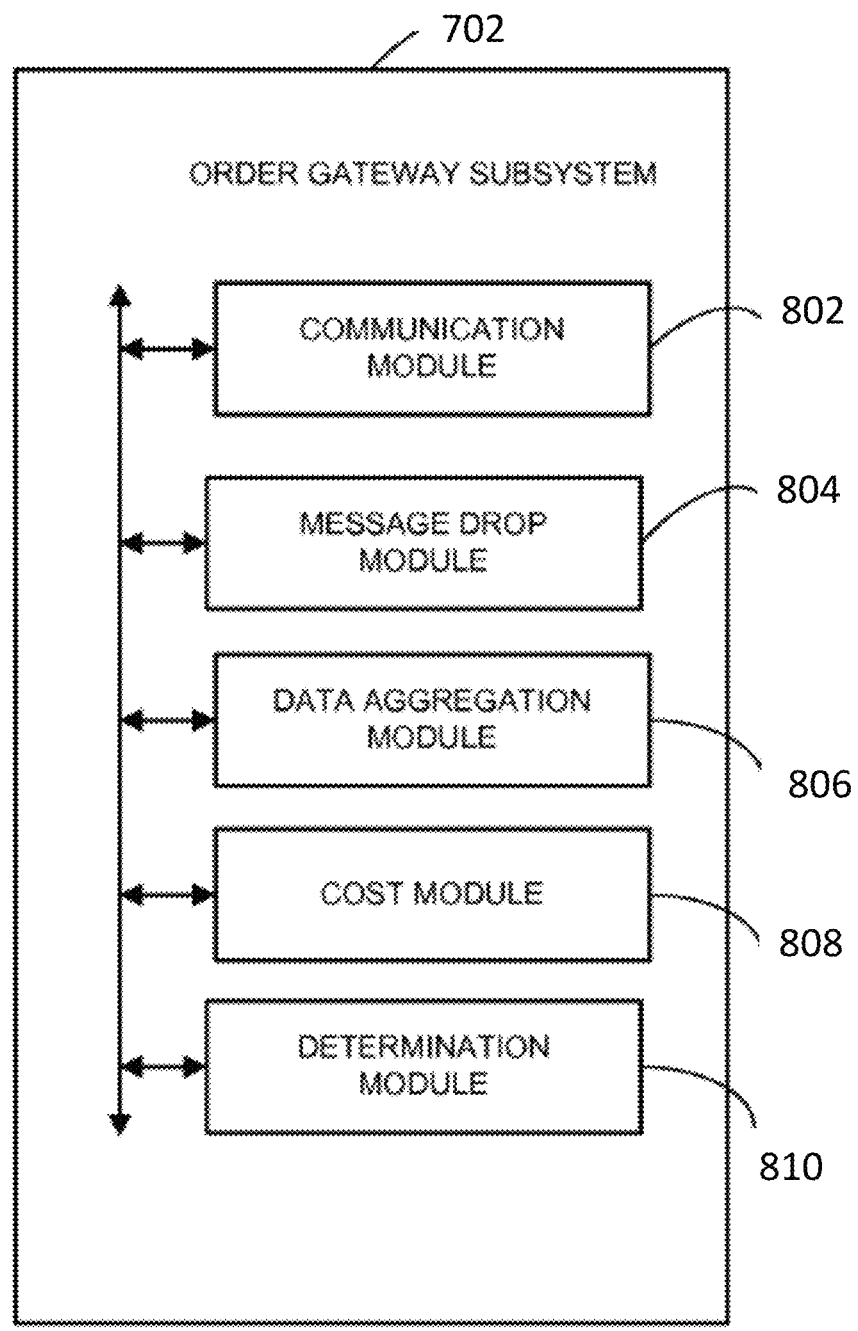
FIG. 8 illustrates one example of an order gateway subsystem.

FIG. 8 illustrates one example of the order gateway subsystem 702. The order gateway subsystem 702 may be deployed in the fulfillment device 612 and/or 614, or may otherwise be used. One or more modules are communicatively coupled and included in the order gateway subsystem 702 to enable communication with the order processing stations 102 and the fulfillment devices 612, 614. The order gateway subsystem 702 may include a communication module 802, a message drop module 804, a data aggregation module 806, a cost module 808, and a determination module 810. In one embodiment, the modules are deployed in memory and executed by a processor or more than one processor coupled to the memory. The functionality contained within the modules 802-810 may be combined into a lesser number of modules, further divided among a greater number of modules, or redistributed among existing modules. Other configurations including the functionality of the modules 802-810 may be used.

The communication module 802 communicatively links the fulfillment device 612 and/or 614 to the network 104. The communication module 802 handles communication of data between two or more data sources using one or more communication protocols such as machine to machine communications and machine to enterprise communications. The message drop module 804 provides storage containment of assigned order messages until they are pulled or downloaded by the fulfillment devices 612, 614. For example, the message drop module 804 utilizes post office protocol (POP) or internet message access protocol (IMAP) for retrieval of the order messages by the fulfillment devices 612, 614. The fulfillment devices 612, 614 may access the message drop module 804 to pull (e.g., download) the order messages assigned to the fulfillment devices 612, 614 at a desired frequency to obtain more prescription orders. In some embodiments, the order gateway subsystem 702 may access the message drop module 804 and push (e.g., send) the message order to the fulfillment devices 612, 614. Furthermore, the order status subsystem 708 may also access the message drop module 804 to change prescription parameters or dispensation preferences in the order message. The order status subsystem 708 may also pause or hold the order message in the message drop module 804, or may cancel or delete the order message in the message drop module 804.

In an example embodiment, the order gateway subsystem 702 contains order messages that are not assigned to a particular fulfillment device 612, 614. The order messages are stored in the message drop module 804 and analyzed by the determination module 810, as explained below.

The order gateway subsystem 702 may include a data aggregation module 806 for aggregating data that includes prescription parameters, dispensation preferences, and dispensary attributes. The data aggregation module 806 may obtain the prescription parameters, dispensation preferences, and dispensary attributes from the order processing station, the fulfillment devices 612, 614, the benefits manager device 108, and/or from the patient data, the client data, and/or the pharmacy data in the database 110. Dispensation preferences may include implementation of corporate policies, such as inclusion of an envelope for remittance if not enrolled in automatic payment, printing of adherence messages and refill reminders. Dispensation preferences may include one or more patient preferences and/or one or more client preferences. Patient preferences that are relevant to the order fulfillment station 108 during fulfillment of the prescription order may include email notifications, specialty caps on vials, personalized refill reminder messages, personalized adherence messages, or the like. Client preferences that are relevant to the order fulfillment station 108 may include specified shipping containers, mail carriers, specialty labels, brail printing capability, etc. Client preferences may also include the requirement that the prescription be fulfilled at the order fulfillment station 108 that allows unions or utilizes only union mail carriers. Client preferences also include client prioritization. That is, prescription orders from patients of certain clients may have a higher priority for fulfillment than other prescription orders. In other words, an age of the order message may be considered by the fulfillment gateway 106 when determining order fulfillment. The age of the order message is determined by the time of generation of the order message where the order message has not been delivered yet. Dispensary attributes are operational characteristics of the fulfillment devices 612, 614. Examples of dispensary attributes may include: for each fulfillment devices 612, 614, inventory level or availability of prescription drugs; fulfillment of specialty drugs (e.g., compounding); inventory level or availability of specialty containers or caps; marking capability of labels, containers or caps; cost based calculations for the prescribed drugs capable of being fulfilled at the fulfillment devices 612, 614; specialty packaging capability; operational cold rooms; added security for class C-2 narcotic prescription drugs; union-only labor; or the like.

The order gateway subsystem may also include a cost module 808 to calculate cost based calculations for the fulfillment devices 612, 614. The data aggregation module 806 and the cost module 808 may be communicatively coupled and included in the order gateway subsystem to enable site selection. The cost based calculations include a calculated cost-to-fill value associated with each prescription drug at each of the fulfillment devices 612, 614. The cost-to-fill value may be stored as a portion of the pharmacy data and updated by the cost module 808. The cost-to-fill value may be the cost to fulfill a prescribed drug based on costs of labor, shipping, and/or materials, for example, at the fulfillment devices 612, 614. Cost for labor, shipping, and materials may be weighted as desired. Cost of materials may include cost of prescription drugs purchased from distributors, as well as prescription drug containers, caps, packaging supplies, or the like. The cost-to-fill value of the prescription drug may vary among the fulfillment devices 612, 614, (e.g., each fulfillment device 612, 614 having its own, but not necessarily unique, cost-to-fill value per prescription drug). For example, if one of the fulfillment devices 612, 614 is highly automated, it may have a lower cost-to-fill value than another of the fulfillment devices 612, 614. More specifically, if the fulfillment device 612 and/or 614 has an automated process to fulfill a type of prescribed drug in place but another fulfillment device 612 and/or 614 requires manual fulfillment, the cost-to-fill may be lower for automated fulfillment.

The cost based calculations, calculated by the cost module 808, may include a maximum variance value for prescription drugs fulfilled by the fulfillment devices 612, 614. In some embodiments, the maximum variance may be preset and stored in memory. In general, the maximum variance value is a maximum variance in the cost-to-fill value that is tolerable to ensure efficient fulfillment of the prescription order. Fulfillment of the prescription order at the fulfillment devices 612 and/or 614 having a cost-to-fill value greater than the lowest cost-to-fill value among multiple fulfillment devices 612, 614 may be acceptable in some circumstances where the maximum variance value is not exceeded. The maximum variance value is exceeded when the cost-to-fill value of the fulfillment devices 612, 614 is greater than a reference cost-to-fill value (e.g., lowest cost-to-fill value among multiple fulfillment devices 612, 614). An example of a circumstance in which the maximum variance is considered is the case of a backlog at one of the fulfillment devices 612, 614. Another example is when client priority (e.g., age) of the order message, causes the selection of fulfillment device 612 or 614 with a higher cost-to-fill value (that does not exceed the reference cost-to-fill value by the maximum variance value) to ensure timely fulfillment.

The order gateway subsystem 702 may include a determination module 810 that may communicate with the data aggregation module 806 and the cost module 808. The determination module 810 utilizes a rule-based site selection process based on prioritization of the prescription parameters, the dispensation preferences, and the dispensary attributes to determine the appropriate fulfillment device 612, 614 to send the order message. The determination module 810 may update its determination upon a sudden price increase in the prescription drug, a reduction in backlog, a change in formulary, or the like. In such a case, the determination module 810 may access the message drop module 804 to update or refresh the selection among the fulfillment devices 612, 614. The determination module 810 may access the message drop module 804 in the event that the order message needs to be reassigned to a different fulfillment device 612 or 614. That is, the determination module 810 may readdress the order message before it is downloaded by the originally assigned fulfillment device 612, 614.

The determination module 810 may accumulate multiple order messages into a batch for delivery to the fulfillment devices 612, 614. The fulfillment devices 612, 614 may request a specific number of order messages in the batch. That is, the fulfillment devices 612, 614 may identify a desired number of order messages in the batch for delivery. In response, the determination module 810 may accumulate no more order messages than the identified desired number.

In the embodiment in which the order messages are stored in the message drop module 804 without assignment to a particular fulfillment device 612, 614, the determination module 810 may determine which order messages are appropriate for delivery to the fulfillment devices 612, 614. The determination may be based on dispensary attributes, such as cost-to-fill values, dispensation preferences (such as maximum variance values), adjudication responses, etc. In response to the fulfillment devices 612, 614 requesting a batch of multiple order messages, the determination module 810 may determine which order messages have the lowest cost-to-fill values. For example, the dispensary attribute of a fulfillment device 612, 614 may include a cost-to-fill value for Fluoxetine 60 mg that is the lowest of all of the multiple fulfillment devices 612, 614. In this case, order messages associated with prescription orders for Fluoxetine 60 mg are delivered from the message drop module 804 to the fulfillment device 612, 614 with the lowest cost-to fill value.

Regardless of whether the order messages are stored in the message drop module 804 as assigned or unassigned, the order messages may be delivered to the fulfillment devices 612, 614 by pushing or pulling. The fulfillment device 612, 614 may access the message drop module 804 to pull (e.g., download) the order messages assigned to the fulfillment device 612, 614 at a desired frequency to obtain more prescription orders. In some embodiments, the order gateway subsystem 702 may access the message drop module 804 and push (e.g. send) the order message to the fulfillment devices 612, 614. Furthermore, the fulfillment devices 612, 614 may request order messages. Examples of sending the order message without a request may include sending a high priority order message to the fulfillment devices 612, 614 or sending the order message at a preset frequency.

In an example embodiment, the fulfillment device 612, 614 that takes delivery of the order messages is an under capacity fulfillment device 612, 614. Under capacity, as used herein, is intended to impart the real-time existence of a less than desired workload or anticipation of a less than desired work load. The determination module 810 may select order messages based on dispensation preferences, such as maximum variance. Specifically, upon receiving a request for a batch of order messages, the determination module 810 may compare the cost-to-fill value for the prescription drug at the requesting fulfillment device 612, 614 with the maximum variance for the prescription drug. If the cost-to-fill value of the requesting fulfillment device 612, 614 does not exceed the lowest cost-to-fill value (attributed to another fulfillment device 612, 614) by the maximum variance value, the order message for the prescription drug is provided to the requesting fulfillment device 612, 614.

The cost module 808 and/or the determination module 810 may adjust the maximum variance value based on dispensation preferences, such as age of order or client priority, or based on dispensary attributes, such as the loss or substantial incapacitation of a fulfillment device 612, 614. Furthermore, the determination module 810 may determine age of the order message based on the time of generating the order message. That is, the order has been generated following an adjudication response, but not yet delivered to the fulfillment device 612, 614. The time of generating the order message may be a prescription parameter of the order message. The determination module 810 may access dispensation preferences, stored locally or at the database 110, and compare the age of the message order with the dispensation preference. In an example embodiment, the dispensation preference may include an age threshold. The age threshold is a threshold that limits the order message's time in storage at the message drop module 804. If the determination module 810 determines that the order message has aged, starting from the time of generating, past the age threshold, the determination module 810 may communicate with the communication module 802. The communication module 802 may send the order message to a fulfillment device 612, 614 to begin fulfillment. The determination module 810 may also select order messages for delivery to the fulfillment device 612, 614 based on age without consideration of age threshold. For example, older order messages are selected before new order messages.

Figure 9:
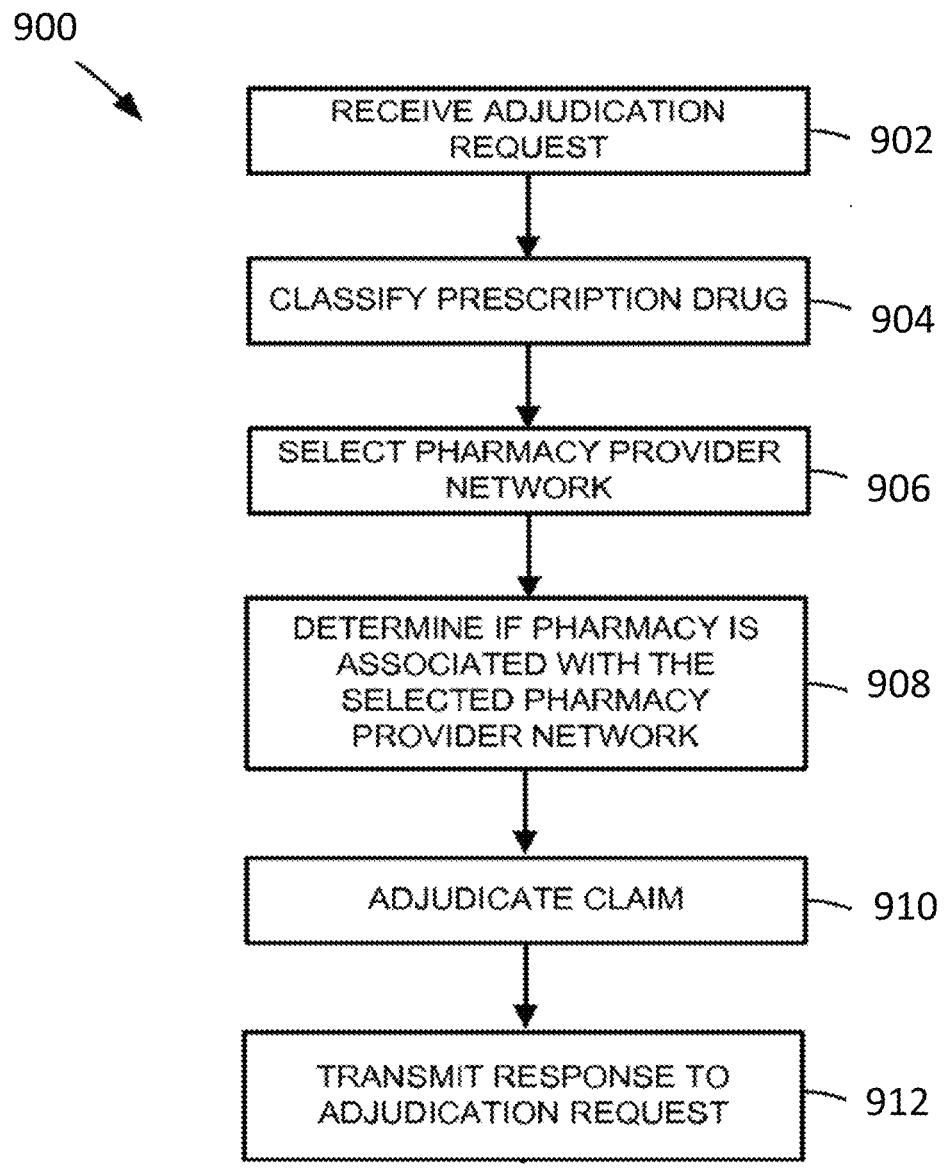
FIG. 9 is a block diagram of a flowchart illustrating a method for maintaining pharmacy provider networks, according to an example embodiment.

FIG. 9 illustrates a method 900 for maintaining pharmacy provider networks, according to an example embodiment. The method 900 may be performed by the pharmacy benefit manager device 108, partially by the pharmacy benefit manager device 108 and partially by the pharmacy device 102, or may be otherwise performed.

An adjudication request may be received at block 902. The adjudication request may be associated with a current adjudication request and/or a previous or historical adjudication request. For example, receiving the adjudication request may include accessing claim adjudication data. Claims adjudication data may be received or retrieved from the database 110. For example, claims adjudication data may be included, at least in part, in the member data 112 included within database 110. In some embodiments, the claims adjudication data may be received from the pharmacy device 102. In some embodiments, an adjudication request may be received from the pharmacy benefits manager device 108. The adjudication request may include a pharmacy claim associated with a member, a prescribed drug, and a pharmacy. In some embodiments, the claims adjudication data may be access through other sources, such as data feeds from different healthcare provider vendors, servers, databases, or the like.

The prescribed drug associated with the adjudication request may be classified at block 904. In some embodiments, the claim adjudication data associated with the member may be analyzed to identify any prescribed drugs associated with the member. The identified prescribed drugs may include newly prescribed drugs, existing prescribed drugs, past prescribed drugs, and the like. The identified prescribed drug may be classified as acute medication or maintenance medication. In some embodiments, the identified prescribed drug may be classified using one, or more than one, classification rules. Classifying the identified prescribed drug as either an acute medication or a maintenance medication may include determining a number of refills (e.g., a number of available refills and/or a number of refills that have been requested) for the prescribed drug. In some embodiments, classifying the prescribed drugs may include comparing the number of refills for the prescribed drugs to a threshold number of refills. In some embodiments, all prescribed drugs may be classified as acute medications by default, and may be classified as maintenance medications when one, or more than one, maintenance medication criterion are met (e.g., a determination of a drug type, a drug classification, a threshold number of fills, a threshold number of available refills, or the like).

In some embodiments, a pharmacy provider network may be selected, at block 906, based on the classified prescribed drug. In some embodiments, if the prescribed drug is classified as an acute medication, then an acute medication pharmacy provider network may be selected. In some embodiments, if the prescribed drug is classified as a maintenance medication, then a maintenance medication pharmacy provider network may be selected.

In some embodiments, the prescribed drug may be associated at block 906 with either an acute medication pharmacy provider network or a maintenance medication pharmacy provider network in response to the classification of the prescribed drug. In some embodiments, the acute medication pharmacy provider network may include a retail pharmacy and/or a mail order pharmacy. In some embodiments, the maintenance medication pharmacy provider network may include a retail pharmacy and/or a mail order pharmacy.

In some embodiments, a determination is made whether the pharmacy associated with the adjudication request is associated with the selected pharmacy provider network at block 908. Determining if the pharmacy associated with the adjudication request (e.g., the pharmacy at which a request to fill a prescription is made by a member) may include accessing acute medication pharmacy network data 114 and/or accessing maintenance medication pharmacy network data 116. If the pharmacy associated with adjudication request is included in the acute medication pharmacy network data 114, it may be determined that the pharmacy associated with the adjudication request is included in the acute medication pharmacy provider network. If the pharmacy associated with the adjudication request is included within the maintenance medication pharmacy network data 116, it may be determined that the pharmacy associated with the adjudication request is included within the maintenance medication pharmacy provider network.

In some embodiments, the pharmacy associated with the adjudication request may be a retail pharmacy. In some embodiments, the pharmacy associated with the adjudication request may be a mail-order pharmacy. In some embodiments, the pharmacy may not be associated with a pharmacy provider network. If the pharmacy associated with the adjudication request is not associated with a pharmacy provider network, one or more pharmacies that are associated with the selected pharmacy provider network may be provided or generated. In some embodiments, the one or more pharmacies that are associated with the selected pharmacy provider network may be provided or identified as a suggested alternative pharmacy.

In some embodiment, if the pharmacy is determined to be associated with the selected pharmacy provider network, (e.g., the prescription is determined to be for an acute medication and the pharmacy is included within an acute medication pharmacy provider network, or the prescription is determined to be for a maintenance medication and the pharmacy is included within a maintenance medication pharmacy provider network) the pharmacy claim associated with the adjudication request may be adjudicated on behalf of the member. In some embodiments, the pharmacy claim associated with the adjudication request may not be adjudicated until a request to proceed with the adjudication is received or approved.

In some embodiments, if the prescription is for a drug classified as a maintenance medication (e.g., if the number of refills for a prescribed drug associated with the adjudication request exceeds a set threshold for number of refills, or based on other classifying criterion) the requested fill and/or any additional refills may need to be refilled at a pharmacy in or associated with the maintenance medication pharmacy provider network (for example, in order for the PBM to receive best pricing for the member). For example, if a prescription has refills beyond the first fill (e.g., a second fill), the member may be required to fill the additional fills at a pharmacy in the maintenance medication pharmacy provider network to obtain best pricing for the member. In some embodiments, the maintenance medication pharmacy provider network may include a subset of pharmacies in the acute medication pharmacy provider network.

In some embodiments, the pharmacy claim may be adjudicated at block 910. For example, the pharmacy claim for the prescription that the member is attempting to fill may be adjudicated, which may in some embodiments include operations such as conducting a DUR relative to the prescription, determining member coverage, etc. In some embodiments, the adjudication module may adjudicate the pharmacy claim for the prescribed drug based on the claim and the pharmacy provider network in which the pharmacy submitting the claim is included. In an embodiment in which the prescription drug may be classified as a maintenance medication and the pharmacy may be determined to be included within an acute medication pharmacy provider network, the claim may be adjudicated using the first set of member benefits (e.g., the set of member benefits for prescriptions for maintenance medications filled at pharmacies included within acute medication pharmacy provider networks).

In some embodiments, a response to the adjudication request may be generated and transmitted at block 912. In some embodiments, the response to the adjudication request may include the classification of the prescribed drug, the selected pharmacy network, the data associated with the adjudication of the pharmacy claim, or any combination thereof. If the pharmacy associated with the adjudication request is not associated with the selected pharmacy provider network, a message stating that the pharmacy is not a part of the selected pharmacy network may be transmitted to the pharmacy device 102 and/or the member device 106. In some embodiments, the response may include a list of suggested or alternative pharmacies associated with the selected pharmacy network may also be included. The response can be included in and/or otherwise communicated with an order or order message that is sent to a fulfillment device for automatically filling the prescription, as described above.

In some embodiments, different member benefits for the prescription under the drug benefit program may be associated with pharmacies included within the acute medication pharmacy provider network and with pharmacies included within the maintenance medication pharmacy provide network. For example, the different benefits for the prescription may include different costs (e.g., co-pay, coverage eligibility, etc.) to the member associated with filling a prescription for a maintenance medication at a pharmacy within the acute medication pharmacy provider network as compared to the costs to the member associated with filling the prescription at a pharmacy within the maintenance medication pharmacy provider. The difference in the member benefits for the prescription under the drug benefit program may motivate the member to seek fills of prescriptions for a maintenance medication at a pharmacy included within the maintenance medication pharmacy provider network.

In some embodiments, the costs associated with the acute medication pharmacy provider network or the maintenance medication pharmacy provider network may include co-pays, reimbursement rate, billed rate, or any combination thereof. In some embodiments, the reimbursement rate for the provider may be the pay rate to the pharmacy provider (e.g. the pharmacy fulfilling the prescription of the member) for purchasing the prescribed drug and dispensing the prescribed drug to the member. In some embodiments, the billed rate to the client or client affiliates is the rate that the client is charged for dispensing the prescribed drug to the member by the pharmacy or provider. In some embodiments, the spread may be the difference between the billed rate to the client and the reimbursement rate for the pharmacy provider.

Other factors that may influence or affect costs associated with pharmacy provider networks may include explicit administrative fees that may be charged, rebates prescribed drug or tasks associated with the process of dispensing the prescribed drug to members, or bulk discount rates for prescribed drugs obtained by providers.

Figure 10:
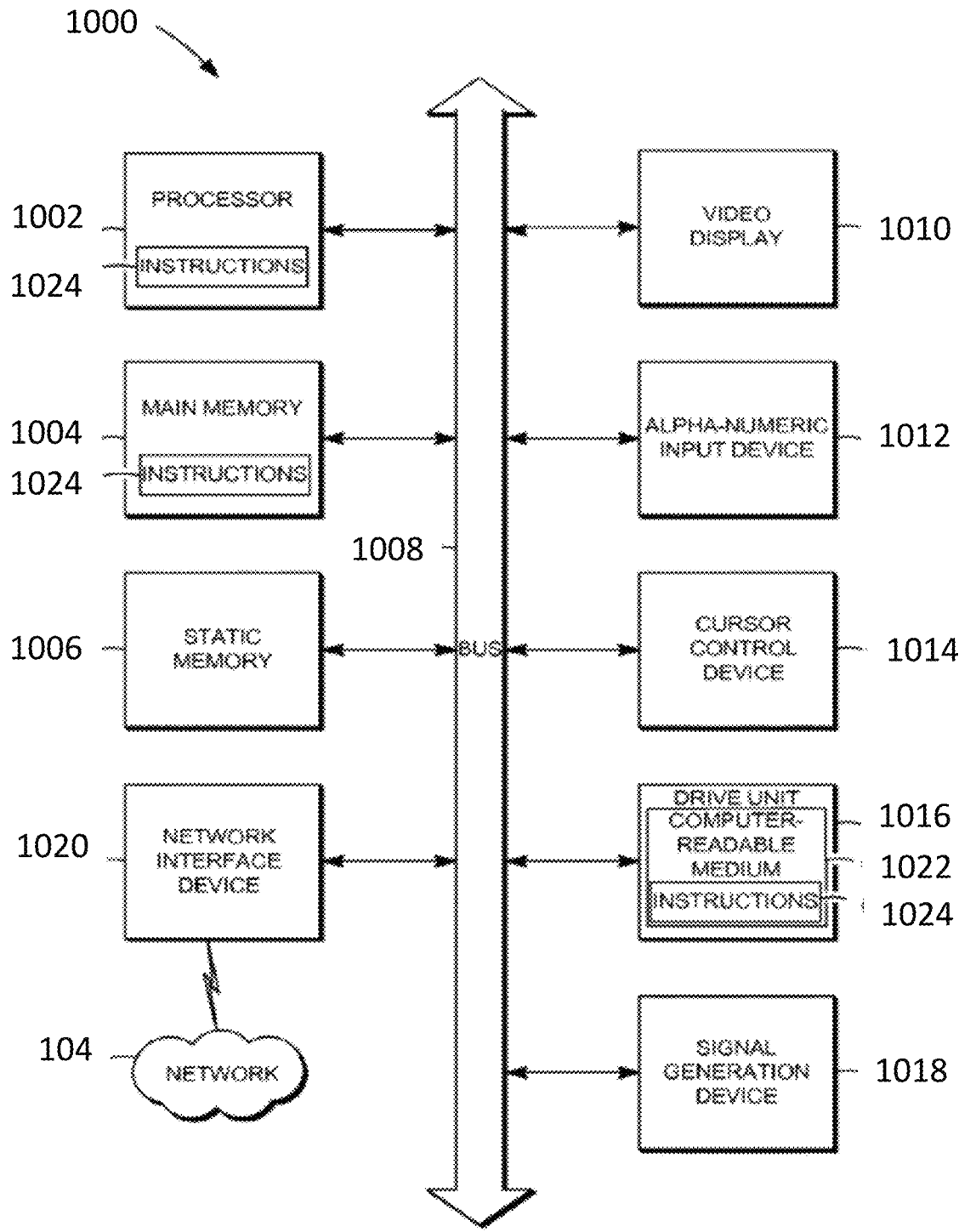
FIG. 10 is a block diagram of a machine in the example form of a computer system within which a set of instructions for causing the machine to perform any one or more of the methodologies discussed herein may be executed.

FIG. 10 shows a block diagram of a machine in the example form of a computer system 1000 within which a set of instructions may be executed causing the machine to perform any one or more of the methods, processes, operations, or methodologies discussed herein. The member device 106 and/or the pharmacy benefit manager device 108 may include the functionality of the one or more computer systems 1000.

In an example embodiment, the machine operates as a standalone device or may be connected (e.g., networked) to other machines. In a networked deployment, the machine may operate in the capacity of a server or a client machine in server-client network environment, or as a peer machine in a peer-to-peer (or distributed) network environment. The machine may be a server computer, a client computer, a personal computer (PC), a tablet PC, a set-top box (STB), a Personal Digital Assistant (PDA), a cellular telephone, a web appliance, a network router, switch or bridge, or any machine capable of executing a set of instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

The example computer system 1000 includes at least one processor 1002 (e.g., a central processing unit (CPU) a graphics processing unit (GPU) or both), a main memory 1004 and a static memory 1006, which communicate with each other via a bus 1008. The computer system 1000 may further include a video display unit 1010 (e.g., a liquid crystal display (LCD) or a cathode ray tube (CRT)). The computer system 1000 also includes an alphanumeric input device 1012 (e.g., a keyboard), a cursor control device 1014 (e.g., a mouse), a drive unit 1016, a signal generation device 1018 (e.g., a speaker), and a network interface device 1020.

The drive unit 1016 includes a computer-readable medium 1022 on which is stored one or more sets of instructions (e.g., software 1024) embodying any one or more of the methodologies or functions described herein. The software 1024 may also reside, completely or at least partially, within the main memory 1004 and/or within the processor(s) 1002 during execution thereof by the computer system 1000, the main memory 1004, and the processor(s) 1002, also constituting computer-readable media. In some embodiments, the computer-readable medium 1022 is a non-transitory computer-readable medium. The software 1024 may further be transmitted or received over the network 104 via the network interface device 1020.

While the computer-readable medium 1022 is shown in an example embodiment to be a single medium, the term "computer-readable medium" should be taken to include a single medium or multiple media (e.g., a centralized or distributed database, and/or associated caches and servers) that store the one or more sets of instructions. The term "computer-readable medium" shall also be taken to include any medium that is capable of storing or encoding a set of instructions for execution by the machine and that cause the machine to perform any one or more of the methodologies of the present invention. The term "computer-readable medium" shall accordingly be taken to include, but not be limited to, solid-state memories, optical media, and magnetic media.

The term "based on" or using, as used herein, reflects an open-ended term that can reflect other elements beyond those explicitly recited.

Certain systems, apparatus, applications, or processes are described herein as including a number of modules. A module may be a unit of distinct functionality that may be presented in software, hardware, or combinations thereof. When the functionality of a module is performed in any part through software, the module includes a computer-readable medium. The modules may be regarded as being communicatively coupled. In some example embodiments, the module includes a processor circuitry that loads instructions from a memory for certain tasks as described herein, e.g., adjudication, prescription fulfillment or others, and is a dedicated machine when loaded with the instructions.

The inventive subject matter may be represented in a variety of different embodiments of which there are many possible permutations.

In one embodiment, claims adjudication data associated with a member and a prescribed drug may be accessed. The prescribed drug associated with the member may be classified as one of an acute medication and a maintenance medication. A pharmacy provider network may be associated with the prescribed drug based on, at least in part, classifying the prescribed drug. It may be determined if a pharmacy associated with the claims adjudication data is included within the pharmacy provider network associated with the prescribed drug. A pharmacy claim may be adjudicated for the prescribed drug based on the claim and the pharmacy provider network.

In an embodiment, a pharmacy claim to adjudicate is received. The pharmacy claim is associated with a member and a prescribed drug may be received. The prescribed drug associated with the member may be classified as a maintenance medication. It may be determined that a pharmacy associated with the request to adjudicate the pharmacy claim is included within an acute medication pharmacy provider network. A warning that a modified set of member benefits are associated with filling the prescribed drug at the pharmacy may be transmitted based on the classification of the prescribed drug as a maintenance medication and a determination that the pharmacy is included within the acute medication pharmacy provider network.

While the methods and systems are generally described herein within the context of acute pharmacy provider networks and maintenance pharmacy provider networks, other types or classification of pharmacy provider network may be made. Additionally, while the method and systems are generally described herein within the context of prescription drugs and pharmacies, the principles herein may be equally applied to claims under drug benefit programs, or other healthcare programs administered by a PBM or a healthcare program provider. Examples of other such programs may include benefits for care, testing, and treatment associated with medication professional visits, medical lab work, hospitals, and clinics.

Thus, methods and systems for maintaining pharmacy provider networks have been described. Although embodiments of the present invention have been described with reference to specific example embodiments, it will be evident that various modifications and changes may be made to these embodiments without departing from the broader spirit and scope of the embodiments of the invention. Accordingly, the specification and drawings are to be regarded in an illustrative rather than a restrictive sense.

The methods described herein do not have to be executed in the order described, or in any particular order. Moreover, various activities described with respect to the methods identified herein can be executed in serial or parallel fashion. Although "End" blocks are shown in the flowcharts, the methods may be performed continuously.

The Abstract of the Disclosure is provided to comply with 37 C.F.R. § 1.72(b), requiring an abstract that will allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter may lie in less than all features of a single disclosed embodiment. Thus, the following claims are hereby incorporated into the Detailed Description, with each claim standing on its own as a separate embodiment.

What is claimed is:

1. A method for communicating over a network to fill a prescription, the method comprising:
retrieving claims adjudication data associated with a member and a prescribed drug stored in a memory;
determining, on one or more processors, whether a number of available fills of the prescribed drug exceeds an acute medication threshold number of the available fills, the acute medication threshold number stored in a database and included in a pharmacy benefit provided to the member;
classifying, using the one or more processors, the prescribed drug associated with the member as an acute medication or a maintenance medication based on determining whether the number of the available fills exceeds the acute medication threshold number and based on a number of requests for fills of the prescribed drug and a duration of treatment of the member using the prescribed drug;
associating, using the one or more processors, the prescribed drug with an acute medication pharmacy provider network or a maintenance medication pharmacy provider network based on classification of the prescribed drug as the acute medication or the maintenance medication;
transitioning the prescribed drug from the maintenance medication pharmacy provider network to the acute medication pharmacy provider network responsive to the prescribed drug previously being associated with the maintenance medication pharmacy provider network;

determining, using the one or more processors, whether a pharmacy associated with the claims adjudication data is included within the acute medication pharmacy provider network;

adjudicating, using the one or more processors, a pharmacy claim for the prescribed drug through the pharmacy responsive to determining that the pharmacy is included within the acute medication pharmacy provider network;

communicating an adjudication response indicative of the pharmacy claim that is adjudicated to an order processing device at a pharmacy filling system via a communication network;

determining which automated dispensing devices of a pharmacy filling system are responsible for filling the prescribed drug associated with the pharmacy claim that is adjudicated based on the adjudication response;

arranging pucks on a pallet using a pallet sizing and pucking device of the pharmacy filling system and based on which of the automated dispensing devices is determined to be responsible for filling the prescribed drug, the pallet sizing and pucking device changing an order in which several medication fills in a queue are to be launched for completion, the pallet sizing and pucking device changing the order in which the medication fills are launched based on the adjudication response;

loading one or more prescription containers into the pucks on the pallet using robotic pickers of a loading device and based on which of the automated dispensing devices is determined to be responsible for filling the prescribed drug;

printing one or more labels for the one or more prescription containers and applying the one or more labels to the one or more prescription containers using the loading device; and automatically filling the prescription at the pharmacy after receipt of the adjudication response using an automated dispensing device dispensing the prescribed drug into one or more of the prescription containers.

2. The method of claim 1, wherein retrieving the claims adjudication data includes receiving an adjudication request from the pharmacy relative to the prescribed drug for the member.

3. The method of claim 1, wherein retrieving the claims adjudication data includes accessing historical claims adjudication data of the member.

4. The method of claim 1, further comprising:
analyzing the claims adjudication data to determine one or more of a drug attribute or a fill attribute associated with the prescribed drug.

5. The method of claim 1, wherein classifying the prescribed drug comprises:
identifying one of a drug identity, a drug type, or a drug category.

6. The method of claim 1, wherein classifying the prescribed drug comprises:
determining that a number of fill requests of the prescribed drug exceeds the acute medication threshold number.

7. The method of claim 1, further comprising:
associating a first set of member benefits with the prescribed drug for the acute medication pharmacy provider network; and associating a second set of the member benefits with the prescribed drug for the maintenance medication pharmacy provider network.

8. The method of claim 1, wherein accessing the claims adjudication data includes accessing historical claims adjudication data of the member.

9. A method for filling a prescription, the method comprising:
receiving, on one or more processors, a pharmacy claim to adjudicate the pharmacy claim associated with a member and a prescribed drug;

selecting an acute medication threshold number of available fills;

communicating the acute medication threshold number of available fills to the one or more processors;

classifying, using the one or more processors, the prescribed drug associated with the member as a maintenance medication based on a determination of whether a number of available fills of the prescribed drug exceeds the acute medication threshold number of available fills;

determining, using the one or more processors, that a pharmacy associated with a request to adjudicate the pharmacy claim is included within an acute medication pharmacy provider network;

communicating, using the one or more processors, a warning that a modified set of member benefits are associated with filling the prescribed drug at the pharmacy based on classification of the prescribed drug as a maintenance medication and a determination that the pharmacy is included within the acute medication pharmacy provider network; and controlling a filling of the prescription for the member at the pharmacy after receipt of an adjudication response associated with the member, the filling of the prescription controlled by communicating an adjudication response indicative of the pharmacy claim that is adjudicated to an order processing device at a pharmacy filling system via a communication network, determining which automated dispensing devices of the pharmacy filling system are responsible for filling the prescribed drug associated with the pharmacy claim that is adjudicated based on the adjudication response, arranging pucks on a pallet using a pallet sizing and pucking device of the pharmacy filling system and based on which of the automated dispensing devices is determined to be responsible for filling the prescribed drug, changing an order in which several medication fills in a queue are to be launched for completion based on the adjudication response, loading one or more prescription containers into the pucks on the pallet using robotic arms of a loading device and based on which of the automated dispensing devices is determined to be responsible for filling the prescribed drug, printing one or more labels for the one or more prescription containers, applying the one or more labels to the one or more containers, and automatically filling the prescription at the pharmacy after receipt of the adjudication response using an automated dispensing device dispensing the prescribed drug into the one or more prescription containers.

10. The method of claim 9, wherein the modified set of member benefits includes an elevated member co-pay.

11. The method of claim 10, wherein determining includes transitioning the prescription from the acute medication pharmacy provider network and a maintenance medication pharmacy provider network when the acute medication threshold number is exceeded and filling the prescription using the maintenance medication pharmacy provider network with a different member benefit than a member benefit at the acute medication pharmacy provider network.

12. The method of claim 11, further comprising:
associating a first set of member benefits with the prescribed drug for the acute medication pharmacy provider network; and
associating a second set of the member benefits with the prescribed drug for the maintenance medication pharmacy provider network.

13. The method of claim 9, wherein retrieving the pharmacy claim includes receiving the request from the pharmacy relative to the prescribed drug for the member.

14. The method of claim 9, wherein classifying the prescribed drug includes accessing historical claims adjudication data of the member.

15. A pharmacy filling system comprising:
a database storing an acute medication threshold number of fills of a medication associated with an acute medication and included in a pharmacy benefit provided to a member;
a benefit manager device retrieving claims adjudication data associated with a member and a prescribed drug, the benefit manager device determining whether a number of available fills of the prescribed drug exceeds the acute medication threshold number, the benefit manager device classifying the prescribed drug associated with the member as an acute medication or a maintenance medication based on determining whether the number of the available fills exceeds the acute medication threshold number and based on a number of requests for fills of the prescribed drug and a duration of treatment of the member using the prescribed drug, the benefit manager device associating the prescribed drug with an acute medication pharmacy provider network or a maintenance medication pharmacy provider network based on classification of the prescribed drug as the acute medication or the maintenance medication, the benefit manager device transitioning the prescribed drug from the maintenance medication pharmacy provider network to the acute medication pharmacy provider network responsive to the prescribed drug previously being associated with the maintenance medication pharmacy provider network,
the benefit manager device determining whether a pharmacy associated with the claims adjudication data is included within the acute medication pharmacy provider network, the benefit manager device adjudicating a pharmacy claim for the prescribed drug through the pharmacy responsive to determining that the pharmacy is included within the acute medication pharmacy provider network;
an order processing device receiving an adjudication response from the benefit manager device via a network, the adjudication response indicative of the pharmacy claim that is adjudicated, the order processing device determining which automated dispensing devices are responsible for filling the prescribed drug associated with the pharmacy claim that is adjudicated based on the adjudication response;
a pallet sizing and pucking device arranging pucks on a pallet and changing an order in which several medication fills in a queue are to be launched for completion based on the adjudication response;
a loading device having robotic pickers, the robotic pickers loading one or more prescription containers into the pucks on the pallet, the loading device printing one or more labels for the one or more prescription containers and applying the one or more labels to the one or more prescription containers using the loading device; and
an automated dispensing device automatically filling the prescribed drug at the pharmacy after receipt of the adjudication response by dispensing the prescribed drug into the one or more prescription containers.

16. The pharmacy filling system of claim 15, wherein the benefit manager receives the claims adjudication data by receiving an adjudication request from the pharmacy relative to the prescribed drug for the member.

17. The pharmacy filling system of claim 15, wherein the benefit manager device retrieves the claims adjudication data by accessing historical claims adjudication data of the member.

18. The pharmacy filling system of claim 15, wherein the benefit manager device analyzes the claims adjudication data to determine one or more of a drug attribute or a fill attribute associated with the prescribed drug.

19. The pharmacy filling system of claim 15, wherein the benefit manager device classifies the prescribed drug by identifying one of a drug identity, a drug type, or a drug category.

20. The pharmacy filling system of claim 15, wherein the benefit manager device classifies the prescribed drug by determining that a number of fill requests of the prescribed drug exceeds the acute medication threshold number.

* * * * *